(12) United States Patent
Koch et al.

(10) Patent No.: US 11,078,185 B2
(45) Date of Patent: Aug. 3, 2021

(54) ***MYCOBACTERIUM TUBERCULOSIS*—THIOREDOXIN REDUCTASE INHIBITOR AS AN ANTITUBERCULAR AGENT**

(71) Applicant: Technische Universität Dortmund, Dortmund (DE)

(72) Inventors: Oliver Koch, Dortmund (DE); Luis Bering, Dortmund (DE)

(73) Assignee: TECHNISCHE UNIVERSITAT DORTMUND, Dortmund (DE)

( * ) Notice: Subject to any disclaimer, the term of this patent is extended or adjusted under 35 U.S.C. 154(b) by 0 days.

(21) Appl. No.: 16/720,659

(22) Filed: Dec. 19, 2019

(65) Prior Publication Data

US 2020/0123130 A1 Apr. 23, 2020

Related U.S. Application Data

(63) Continuation of application No. PCT/EP2018/066768, filed on Jun. 22, 2018.

(30) Foreign Application Priority Data

Jul. 4, 2017 (EP) ..................................... 17179568

(51) Int. Cl.
*C07D 401/12* (2006.01)
*A61P 31/06* (2006.01)
*C07D 215/44* (2006.01)

(52) U.S. Cl.
CPC ............ *C07D 401/12* (2013.01); *A61P 31/06* (2018.01); *C07D 215/44* (2013.01)

(58) Field of Classification Search
CPC .................................................... C07D 401/12
USPC ....................................................... 546/159
See application file for complete search history.

(56) References Cited

PUBLICATIONS

Babulova et al, Ceskoslova. Akd. Ved. Brastilava, Czech. Arzneimittel-Forschung (1963), 13, pp. 412-414.*
King, Med. Chem. Principle and Practice (1994) pp. 206-208.*
PCT International Preliminary Report on Patentability dated Jan. 7, 2020, (Application No. PCT/EP2018/066768).
Koch, et al., 2013, pp. 4849-4859, Journal of Medicinal Chemistry (XP-002774772), Identification of *M. tuberculosis* Thioredoxin Reductase Inhibitors Based on High-Throughput Docking Using Constraints.
P K Desai, et al., Indian Journal of Chemistry, vol. 35B, Aug. 1996, pp. 871-873, Quinoline Derivatives as Antitubercular/Antibacterial Agents.
Dr. R. H. Slater, Journal Homepage, Jan. 1, 1930, pp. 1209-1215 (XP-002774771), CIII.—Quinoline Compounds Containing Arsenic. Part I. Synthesis of 6-Methoxyquinoline Derivatives of Aminophenylarsinic Acids.
Dr. R. H. Slater, Journal Homepage, Jan. 1, 1931, pp. 107-118, Quinoline Compounds Containing Arsenic, Part II.
Misra, et al., Sep. 1979, pp. 262-264, Indian Journal of Chemistry, Synthesis of New Substituted Quinolines & Study of Their Effect on the Tobacco Mosaic Virus.
Gustafsson, et al., 2016, Journal Homepage, pp. 1265-1271, Ebselen and Analogs as Inhibitors of Bacillus Anthracis Thioredoxin Reductase and Bactericidal Antibacterials Targeting *bacillus* Species, *Staphylococcus aureus* and *Mycobacterium tuberculosis*.
Jaeger, et al., 2004, Archives of Biochemistry and Biophysics, pp. 182-191, Multiple Thioredoxin-Mediated Routes to Detoxify Hydroperoxides in *Mycobacterium tuberculosis*.
Lu, et al., The FASEB Journal, Research Communication, Nov. 21, 2019, Inhibition of Bacterial Thioredoxin Reductase: an Antibiotic Mechanism Targeting Bacteria Lacking Glutathione.

* cited by examiner

*Primary Examiner* — Taofiq A Solola
(74) *Attorney, Agent, or Firm* — The Dobrusin Law Firm, P.C.

(57) ABSTRACT

The invention relates to *Mycobacterium tuberculosis*-thioredoxin reductase inhibitors, processes for the preparation thereof, drugs containing said compounds, and the use of said compounds for manufacturing drugs.

6 Claims, 3 Drawing Sheets

*MYCOBACTERIUM TUBERCULOSIS*—THIOREDOXIN REDUCTASE INHIBITOR AS AN ANTITUBERCULAR AGENT

The invention relates to *Mycobacterium tuberculosis* thioredoxin reductase inhibitors, processes for the preparation thereof, medicaments containing said compounds and the use of said compounds for manufacturing medicaments.

*Tuberculosis* is a bacterial disease that causes death in around 1.5 million people every year, especially people in developing countries and people with a weakened immune system (e.g. HIV patients). Antitubercular agents currently used in therapy are for the most part over 50 years old. In view of the necessary 6-month therapy, the development of resistance is foreseeable. The first extremely resistant strains have already appeared in industrialized countries. The pathogens of *tuberculosis, Mycobacterium tuberculosis* and other types of mycobacteria, are recognized and absorbed (phagocytosed) by the macrophages of the immune system, but they are not digested in the macrophages due to the particular nature of their cell wall, but can survive in the macrophages. The treatment of *tuberculosis* is very time-consuming and tedious, and the development of antibiotic-resistant strains will become an important issue in the future, as with other bacterial infections. The particular challenge in the development of novel antibiotics against *tuberculosis* is that although these antibiotics must penetrate the macrophages and kill off the bacteria, they must not harm the macrophages themselves.

*Mycobacterium tuberculosis* thioredoxin reductase (MtTrxR) and *Mycobacterium tuberculosis* thioredoxin reductase inhibitors are known in the prior art.

Lin et al., (2016), "*Mycobacterium tuberculosis* Thioredoxin Reductase Is Essential for Thiol Redox Homeostasis but Plays a Minor Role in Antioxidant Defense", PloS Pathog 12 (6), discloses various aspects of *Mycobacterium tuberculosis* thioredoxin reductase.

Furthermore, Koch, O., et al. (2013), "Identification of *M. tuberculosis* thioredoxin reductase inhibitors based on high-throughput docking using constraints", J. Med. Chem. 56: 4849-59, 2013, discloses thioredoxin reductase as a potential target for the development of novel anti-tubercular agents. The most promising compound or the most promising *Mycobacterium tuberculosis* thioredoxin reductase inhibitor was the aminoquinoline 1 with an $IC_{50}$ value of 12.5 μM (according to T. Jäger, H. Budde, L. Flohé, U. Menge, M Singh, M. Trujillo, R. Radi, Arch. Biochem. Biophys. 2004, 423, 182-191).

Further, in connection with thioredoxin reductase inhibitors, reference is made to Gustafsson T N, Osman H, Werngren J, Hoffner S, Engman L, Holmgren A, "Ebselen and analogues as inhibitors of *Bacillus anthracis* thioredoxin reductase and bactericidal antibacterials targeting *Bacillus* species, *Staphylococcus aureus* and *Mycobacterium tuberculosis*", Biochim Biophys Acta. 2016 June; 1860 (6):1265-71.

However, the known compounds are not satisfactory in every respect and there is a need for further compounds with comparable or better properties. This object is achieved by the subject matter of the patent claims.

It has surprisingly been found that the compounds according to the invention show a clear structure-activity relationship to the growth inhibition of *Mycobacterium tuberculosis* in infected human macrophages without having a recognizable detrimental effect on the macrophages. Furthermore, initial findings indicate that the compounds according to the invention are also effective against resistant strains and bacteria such as *Staphylococcus aureus.*

FIG. 1 is directed to the antimycobacterial activity of compounds 2, 8 and 68 according to the invention.

FIG. 2 is directed to the antimycobacterial activity of compound 68 according to the invention against *Mycobacterium tuberculosis* strain H37Rv in infected human macrophages.

FIG. 3 is directed to the cytotoxic activity of compound 68 according to the invention against human macrophages.

The invention relates in a first aspect to compounds of general formula (1), (1)

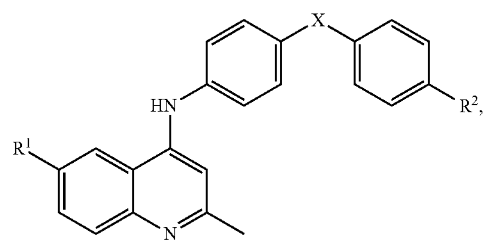

wherein $R_1$ and $R_2$ are each independently selected from the group consisting of —H, —F, —Cl, —Br, —I, —CN, —$NO_2$, —CHO, —$R_0$, —C(═O)$R_0$, —C(═O)H, —C(═O)—OH, —C(═O)O$R_0$, —C(═O)$NH_2$, —C(═O)NH$R_0$, —C(═O)N$(R_0)_2$, —OH, —O$R_0$, —OC(═O)H, —OC(═O)$R_0$, —OC(═O)O$R_0$, —OC(═O)NH$R_0$, —OC(═O)N$(R_0)_2$, —SH, —S$R_0$, —$SO_3$H, —S(═O)$_{1-2}$—$R_0$, —S(═O)$_{1-2}$N$H_2$, —$NH_2$, —NH$R_0$, —N$(R_0)_2$, —$N^+(R_0)_3$, —$N^+(R_0)_2O^-$, —NHC(═O)$R_0$, —NHC(═O)O$R_0$, —NHC(═O)$NH_2$, —NHC(═O)NH$R_0$ and —NHC(═O)N$(R_0)_2$;

X is —$CH_2$—, —S(═O)$_2$— or —C(═O)—;

wherein

"aliphatic" is in each case a branched or unbranched, saturated or mono- or polyunsaturated, unsubstituted or mono- or polysubstituted, aliphatic hydrocarbon radical;

"cycloaliphatic" is in each case a saturated or mono- or polyunsaturated, unsubstituted or mono- or polysubstituted, alicyclic, mono- or multicyclic hydrocarbon radical, the number of ring carbon atoms of which is preferably in the stated range (i.e. "$C_{3-8}$-" cycloaliphatic preferably has 3, 4, 5, 6, 7 or 8 ring carbon atoms);

wherein with respect to "aliphatic" and "cycloaliphatic", "mono- or polysubstituted" is understood to mean single or multiple substitution of one or more hydrogen atoms, e.g. single, double, triple or complete substitution by substituents mutually independently selected from the group consisting of —F, —Cl, —Br, —I, —CN, —$NO_2$, —CHO, ═O, —$R_0$, —C(═O)$R_0$, —C(═O)H, —C(═O)OH, —C(═O)O$R_0$, —C(═O)$NH_2$, —C(═O)NH$R_0$, —C(═O)N$(R_0)_2$, —OH, —O$R_0$, —OC(═O)H, —OC(═O)$R_0$, —OC(═O)O$R_0$, —OC(═O)NH$R_0$, —OC(═O)N$(R_0)_2$, —SH, —S$R_0$, —$SO_3$H, —S(═O)$_{1-2}$—$R_0$, —S(═O)$_{1-2}$N$H_2$, —$NH_2$, —NH$R_0$, —N$(R_0)_2$, —$N^+(R_0)_3$, —$N^+(R_0)_2O^-$, —NHC(═O)$R_0$, —NHC(═O)O$R_0$, —NHC(═O)$NH_2$, —NHC(═O)—NH$R_0$, —NH—C(═O)N$(R_0)_2$, —Si$(R_0)_3$ and —PO(O$R_0$)$_2$;

"aryl" is independently in each case a carbocyclic ring system having at least one aromatic ring, but without heteroatoms in said ring, wherein the aryl radicals may optionally be condensed with further saturated, (partially) unsaturated or aromatic ring systems and each aryl radical may be unsubstituted or mono- or polysubstituted, wherein the aryl substituents may be the same or different and in any desired and possible position of the aryl;

"heteroaryl" is a 5-, 6- or 7-membered cyclic aromatic radical comprising 1, 2, 3, 4 or 5 heteroatoms, wherein the heteroatoms are the same or different nitrogen, oxygen or sulfur, and the heterocycle may be unsubstituted or mono- or polysubstituted; wherein in the case of substitution on the heterocycle, the substituents may be the same or different and in any desired and possible position of the heteroaryl; and wherein the heterocycle may also be part of a bi- or polycyclic system;

wherein with respect to "aryl" and "heteroaryl", "mono- or polysubstituted" is understood to mean the single or multiple substitution of one or more hydrogen atoms of the ring system by substituents selected from the group consisting of —F, —Cl, —Br, —I, —CN, —$NO_2$, —CHO, =O, —$R_0$, —C(=O)$R_0$, —C(=O)H, —C(=O)OH, —C(=O)O$R_0$, —C(=O)$NH_2$, —C(=O)NH$R_0$, —C(=O)—N($R_0$)$_2$, —OH, —O($CH_2$)$_{1-2}$O—, —O$R_0$, —OC(=O)H, —OC(=O)$R_0$, —OC(=O)O$R_0$, —OC(=O)NH$R_0$, —OC(=O)N($R_0$)$_2$, —SH, —S$R_0$, —$SO_3$H, —S(=O)$_{1-2}$—$R_0$, —S(=O)$_{1-2}$$NH_2$, —$NH_2$, —NH$R_0$, —$N^+$($R_0$)$_2$, —$N^+$($R_0$)$_3$, —$N^+$($R_0$)$_2$$O^-$, —NHC(=O)$R_0$, —NHC(=O)O$R_0$, —NH—C(=O)$NH_2$, —NHC(=O)NH$R_0$, —NHC(=O)N($R_0$)$_2$, —Si($R_0$)$_3$ or —PO(O$R_0$)$_2$; wherein N-ring atoms optionally present may in each case be oxidized;

$R_0$ is each independently —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl;

or a physiologically acceptable salt thereof.

"Each independently" in connection with $R_0$ is to be understood that a limitation of the definition of $R_0$ in the context of a preferred embodiment and with respect to a particular radical does not mean that the definition of $R_0$ with respect to any other radical is (analogously) limited unless it is expressly stated that this is the case. Furthermore, any reference to "aliphatic", "cycloaliphatic", "aryl" and "heteroaryl" in the context of a preferred embodiment is to be understood that these are unsubstituted or mono- or polysubstituted, unless it is expressly stated that this is not the case. Furthermore, the definition of "mono- or polysubstituted" in connection with the generic (e.g. "-aryl") also includes the corresponding substitution of the specific (e.g. "-phenyl"), unless it is expressly stated that this is not the case.

The compounds according to the invention show good inhibitory activity towards MtTrxR. In a preferred embodiment, the compounds according to the invention have an $IC_{50}$ value according to Lu et al. from 0.10 to 10.00 μM. Methods for determining the $IC_{50}$ value according to Lu et al. are known to those skilled in the art. Reference is made in this respect to J. Lu, A. Vlamis-Gardikas, K. Kandasamy, R. Zhao, T. N. Gustafsson, L. Engstrand, S. Hoffner, L. Engman, A. Holmgren, FASEB J. 2013, 27, 1394-1403.

Preferably, $R^1$ and $R^2$ are each independently selected from the group consisting of —H, —F, —Cl, —Br, —I, —$R_0$, —C(=O)$R_0$, —C(=O)O$R_0$, —C(=O)NH$R_0$, —C(=O)N($R_0$)$_2$, —O$R_0$, —OC(=O)$R_0$, —OC(=O)O$R_0$, —OC(=O)NH$R_0$, —OC(=O)N($R_0$)$_2$, —S$R_0$, —S(=O)$_{1-2}$—$R_0$, —$NH_2$, —NH$R_0$, —N($R_0$)$_2$, —$N^+$($R_0$)$_3$, —$N^+$($R_0$)$_2$$O^-$, —NHC(=O)$R_0$, —NHC(=O)O$R_0$, —NHC(=O)$NH_2$, —NHC(=O)NH$R_0$ and —NHC(=O)N($R_0$)$_2$; where $R_0$ is each independently —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl or —$C_{1-8}$-aliphatic-heteroaryl.

In a further preferred embodiment, X is —$CH_2$— or —S(=O)$_2$—; $R^1$ is selected from the group consisting of —$R_0$, —C(=O)$R_0$, —C(=O)O$R_0$, —C(=O)NH$R_0$, —C(=O)N($R_0$)$_2$, —O$R_0$, —OC(=O)$R_0$, —OC(=O)O$R_0$, —OC(=O)NH$R_0$ and —OC(=O)N($R_0$)$_2$; where $R_0$ is each independently —$C_{1-8}$-aliphatic, -aryl, -heteroaryl, —$C_{1-8}$-aliphatic-aryl or —$C_{1-8}$-aliphatic-heteroaryl; and $R^2$ is selected from the group consisting of —$NH_2$, —NH$R_0$, —N($R_0$)$_2$, —$N^+$($R_0$)$_3$ and —$N^+$($R_0$)$_2$$O^-$; where $R_0$ is each independently —$CH_3$, —C(=O)$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2$CH($CH_3$)$_2$, —C($CH_3$)$_3$, —$CH_2CH_2CH_2CH_2CH_3$, —$CH_2CH_2CH_2CH_2CH_2CH_3$, —CH=$CH_2$, —C≡CH, —$CH_2$CH=$CH_2$, —CH=CH—$CH_3$, —$CH_2$C≡CH, —C≡C$CH_3$, —CH=CHCH=$CH_2$, in each case unsubstituted, —$C_{3-12}$-cycloaliphatic, -aryl, -heteroaryl or —$C_{1-8}$-aliphatic-$C_{3-12}$-cycloaliphatic; or X is —C(=O)—; $R^1$ is selected from the group consisting of —$R_0$, —C(=O)$R_0$, —C(=O)O$R_0$, —C(=O)NH$R_0$, —C(=O)N($R_0$)$_2$, —O$R_0$, —OC(=O)$R_0$, —OC(=O)O$R_0$, —OC(=O)NH$R_0$ and —OC(=O)N($R_0$)$_2$; where $R_0$ is each independently —$C_{1-8}$-aliphatic, -aryl, -heteroaryl, —$C_{1-8}$-aliphatic-aryl or —$C_{1-8}$-aliphatic-heteroaryl; and $R^2$ is selected from the group consisting of —$NH_2$, —NH$R_0$, —N($R_0$)$_2$, —$N^+$($R_0$)$_3$ and —$N^+$($R_0$)$_2$$O^-$; where $R_0$ is each independently -pyrrolyl, -indolyl, -furyl, -benzofuranyl, -thienyl, -benzothienyl, -benzothiadiazolyl, -benzooxadiazolyl, -benzothiazolyl, -benzooxazolyl, -benzotriazolyl, -benzodioxolanyl, -benzodioxanyl, -phthalazinyl, -pyrazolyl, -imidazolyl, -thiazolyl, -oxazolyl, -isoxazoyl, -pyridinyl, -pyridazinyl, -pyrazinyl, -pyranyl, -indazolyl, -purinyl, -indolizinyl, -quinolinyl, -isoquinolinyl, -quinazolinyl, -carbazolyl, -phenazinyl, -phenothiazinyl, -oxadiazolyl, —$C_{3-12}$-cycloaliphatic, -aryl or —$C_{1-8}$-aliphatic-$C_{3-12}$-cycloaliphatic.

In a further preferred embodiment, X is —$CH_2$— or —S(=O)$_2$—; $R^1$ is selected from the group consisting of —$R_0$, —O$R_0$, —OC(=O)$R_0$, —OC(=O)O$R_0$, —OC(=O)NH$R_0$ and —OC(=O)N($R_0$)$_2$; where $R_0$ is each independently —$CH_3$, —C(=O)$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2$CH($CH_3$)$_2$, —C($CH_3$)$_3$, —$CH_2CH_2CH_2CH_2CH_3$, —$CH_2CH_2CH_2CH_2CH_2CH_3$, —CH=$CH_2$, —C≡CH, —$CH_2$CH=$CH_2$, —CH=CH—$CH_3$, —$CH_2$C≡CH, —C≡C$CH_3$ and —CH=CHCH=$CH_2$, in each case unsubstituted; and $R^2$ is selected from the group consisting of —$NH_2$, —NH$R_0$, —N($R_0$)$_2$, —$N^+$($R_0$)$_3$ and —$N^+$($R_0$)$_2$$O^-$; where $R_0$ is each independently —$CH_3$, —C(=O)$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2$CH($CH_3$)$_2$, —C($CH_3$)$_3$, —$CH_2CH_2CH_2CH_2CH_3$, —$CH_2CH_2CH_2CH_2CH_2CH_3$, —CH=$CH_2$, —C≡CH, —$CH_2$CH=$CH_2$, —CH=CH—$CH_3$, —$CH_2$C≡CH, —C≡C$CH_3$, —CH=CHCH=$CH_2$, in each case unsubstituted, -aryl or -heteroaryl; or X is —C(=O)—; $R^1$ is selected from the group consisting of —$R_0$, —O$R_0$, —OC(=O)$R_0$, —OC(=O)O$R_0$, —OC(=O)NH$R_0$ and —OC(=O)N($R_0$)$_2$; where $R_0$ is each independently —$CH_3$, —C(=O)$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2$CH($CH_3$)$_2$, —C($CH_3$)$_3$, —$CH_2CH_2CH_2CH_2CH_3$, —$CH_2CH_2CH_2CH_2CH_2CH_3$, —CH=$CH_2$, —C≡CH, —$CH_2$CH=$CH_2$, —CH=CH—$CH_3$, —$CH_2$C≡CH, —C≡C$CH_3$ and —CH=CHCH=$CH_2$, in each case unsubstituted; and $R^2$ is selected from the group consisting of —$NH_2$, —$NHR_0$, —$N(R_0)_2$, —$N^+(R_0)_3$ and —$N^+(R_0)_2O^-$; where $R_0$ is each independently -pyrrolyl, -indolyl, -furyl, -benzofuranyl, -thienyl, -benzothienyl, -benzothiadiazolyl, -benzooxadiazolyl, -benzothiazolyl, -benzooxazolyl, -benzotriazolyl, -benzodioxolanyl, -benzodioxanyl, -phthalazinyl, -pyrazolyl, -imidazolyl, -thiazolyl, -oxazolyl, -isoxazoyl, -pyridinyl, - pyridazinyl, -pyrazinyl, -pyranyl, -indazolyl, -purinyl, -indolizinyl, -quinolinyl, -isoquinolinyl, -quinazolinyl, -carbazolyl, -phenazinyl, -phenothiazinyl or -oxadiazolyl.

In a further preferred embodiment, X is —$CH_2$— or —$S(=O)_2$—; $R^1$ is selected from the group consisting of —$R_0$, —$OR_0$, —$OC(=O)R_0$, —$OC(=O)OR_0$, —$OC(=O)NHR_0$ and —$OC(=O)N(R_0)_2$; where $R_0$ is each independently —$CH_3$, —$C(=O)CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2CH_2CH_2CH_3$, —$CH_2CH_2CH_2CH_2CH_3$, —$CH=CH_2$, —$C\equiv CH$, —$CH_2CH=CH_2$, —$CH=CH-CH_3$, —$CH_2C\equiv CH$, —$C\equiv CCH_3$ and —$CH=CHCH=CH_2$, in each case unsubstituted; and $R^2$ is selected from the group consisting of —$NH_2$, —$NHR_0$, —$N(R_0)_2$, —$N^+(R_0)_3$ and —$N^+(R_0)_2O^-$; where $R_0$ is each independently —$CH_3$, —$C(=O)CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2CH_2CH_2CH_3$, —$CH_2CH_2CH_2CH_2CH_3$, —$CH=CH_2$, —$C\equiv CH$, —$CH_2CH=CH_2$, —$CH=CH-CH_3$, —$CH_2C\equiv CH$, —$C\equiv CCH_3$, —$CH=CHCH=CH_2$, in each case unsubstituted, -phenyl, -naphthyl, -anthracenyl, -phenanthrenyl, -fluoranthenyl, -fluorenyl, -indanyl, -tetralinyl, -pyrrolyl, -indolyl, -furyl, -benzofuranyl, -thienyl, -benzothienyl, - benzothiadiazolyl, -benzooxadiazolyl, -benzothiazolyl, -benzooxazolyl, -benzotriazolyl, -benzodioxolanyl, -benzodioxanyl, -phthalazinyl, -pyrazolyl, -imidazolyl, -thiazolyl, -oxazolyl, -isoxazoyl, -pyridinyl, -pyridazinyl, pyrimidinyl, -pyrazinyl, -pyranyl, -indazolyl, -purinyl, -indolizinyl, -quinolinyl, -isoquinolinyl, -quinazolinyl, -carbazolyl, -phenazinyl, -phenothiazinyl or -oxadiazolyl; or X is —$C(=O)$—; $R^1$ is selected from the group consisting of —$R_0$, —$OR_0$, —$OC(=O)R_0$, —$OC(=O)OR_0$, —$OC(=O)NHR_0$ and —$OC(=O)N(R_0)_2$; where $R_0$ is each independently —$CH_3$, —$C(=O)CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2CH_2CH_2CH_2CH_3$, —$CH_2CH_2CH_2CH_2CH_3$, —$CH=CH_2$, —$C\equiv CH$, —$CH_2CH=CH_2$, —$CH=CH-CH_3$, —$CH_2C\equiv CH$, —$C\equiv CCH_3$ and —$CH=CHCH=CH_2$, in each case unsubstituted; and $R^2$ is selected from the group consisting of —$NH_2$, —$NHR_0$, —$N(R_0)_2$, —$N^+(R_0)_3$ and —$N^+(R_0)_2O^-$; where $R_0$ is each independently -pyrrolyl, -indolyl, - furyl, -benzofuranyl, -thienyl, -benzothienyl, -benzothiadiazolyl, -benzooxadiazolyl, -benzothiazolyl, -benzooxazolyl, -benzotriazolyl, -benzodioxolanyl, -benzodioxanyl, -phthalazinyl, -pyrazolyl, -imidazolyl, -thiazolyl, - oxazolyl, -isoxazoyl, -pyridinyl, -pyridazinyl, -pyrazinyl, -pyranyl, -indazolyl, -purinyl, -indolizinyl, -quinolinyl, -isoquinolinyl, -quinazolinyl, -carbazolyl, -phenazinyl, -phenothiazinyl or -oxadiazolyl.

In a further preferred embodiment, X is —$CH_2$— or —$S(=O)_2$—; $R^1$ is selected from the group consisting of —$R_0$, —$OR_0$, —$OC(=O)R_0$, —$OC(=O)OR_0$, —$OC(=O)NHR_0$ and —$OC(=O)N(R_0)_2$; where $R_0$ is each independently —$CH_3$, —$C(=O)CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2CH_2CH_2CH_2CH_3$, —$CH_2CH_2CH_2CH_2CH_3$, —$CH=CH_2$, —$C\equiv CH$, —$CH_2CH=CH_2$, —$CH=CH-CH_3$, —$CH_2C\equiv CH$, —$C\equiv CCH_3$ and —$CH=CHCH=CH_2$, in each case unsubstituted; and $R^2$ is selected from the group consisting of —$NH_2$, —$NHR_0$, —$N(R_0)_2$, —$N^+(R_0)_3$ and —$N^+(R_0)_2O^-$; where $R_0$ is each independently —$CH_3$, —$C(=O)CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2CH_2CH_2CH_2CH_3$, —$CH_2CH_2CH_2CH_2CH_3$, —$CH=CH_2$, —$C\equiv CH$, —$CH_2CH=CH_2$, —$CH=CH-CH_3$, —$CH_2C\equiv CH$, —$C\equiv CCH_3$, —$CH=CHCH=CH_2$, in each case unsubstituted, -phenyl, -naphthyl, -anthracenyl, -phenanthrenyl, -fluoranthenyl, -fluorenyl, -indanyl, -tetralinyl, -pyrrolyl, -indolyl, -furyl, -benzofuranyl, -thienyl, -benzothienyl, - benzothiadiazolyl, -benzooxadiazolyl, -benzothiazolyl, -benzooxazolyl, -benzotriazolyl, -benzodioxolanyl, -benzodioxanyl, -phthalazinyl, -pyrazolyl, -imidazolyl, -thiazolyl, -oxazolyl, -isoxazoyl, -pyridinyl, -pyridazinyl, pyrimidinyl, -pyrazinyl, -pyranyl, -indazolyl, -purinyl, -indolizinyl, -quinolinyl, -isoquinolinyl, -quinazolinyl, -carbazolyl, -phenazinyl, -phenothiazinyl or -oxadiazolyl; or X is —$C(=O)$—; $R^1$ is selected from the group consisting of —$R_0$, —$OR_0$, —$OC(=O)R_0$, —$OC(=O)OR_0$, —$OC(=O)NHR_0$ and —$OC(=O)N(R_0)_2$; where $R_0$ is each independently —$CH_3$, —$C(=O)CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2CH_2CH_2CH_2CH_3$, —$CH_2CH_2CH_2CH_2CH_3$, —$CH=CH_2$, —$C\equiv CH$, —$CH_2CH=CH_2$, —$CH=CH-CH_3$, —$CH_2C\equiv CH$, —$C\equiv CCH_3$ and —$CH=CHCH=CH_2$, in each case unsubstituted; and $R^2$ is selected from the group consisting of —$NH_2$, —$NHR_0$, —$N(R_0)_2$, —$N^+(R_0)_3$ and —$N^+(R_0)_2O^-$; where $R_0$ is each independently -pyrrolyl, -indolyl, - furyl, -benzofuranyl, -thienyl, -benzothienyl, -benzothiadiazolyl, -benzooxadiazolyl, -benzothiazolyl, -benzooxazolyl, -benzotriazolyl, -benzodioxolanyl, -benzodioxanyl, -phthalazinyl, -pyrazolyl, -imidazolyl, -thiazolyl, -oxazolyl, -isoxazoyl, -pyridinyl, -pyridazinyl, -pyrazinyl, -pyranyl, -indazolyl, -purinyl, -indolizinyl, -quinolinyl, -isoquinolinyl, -quinazolinyl, -carbazolyl, -phenazinyl, -phenothiazinyl or -oxadiazolyl; and is understood to mean -phenyl, -naphthyl, -anthracenyl, -phenanthrenyl, -fluoranthenyl, -fluorenyl, -indanyl, -tetralinyl, -pyrrolyl, -indolyl, -furyl, -benzofuranyl, -thienyl, -benzothienyl, - benzothiadiazolyl, -benzooxadiazolyl, -benzothiazolyl, -benzooxazolyl, -benzotriazolyl, -benzodioxolanyl, -benzodioxanyl, -phthalazinyl, -pyrazolyl, -imidazolyl, -thiazolyl, -oxazolyl, -isoxazoyl, -pyridinyl, -pyridazinyl, pyrimidinyl, -pyrazinyl, -pyranyl, -indazolyl, -purinyl, -indolizinyl, -quinolinyl, -isoquinolinyl, -quinazolinyl, -carbazolyl, -phenazinyl, -phenothiazinyl and -oxadiazolyl are each mutually independently unsubstituted or monosubstituted by substituents selected from the group consisting of —F, —Cl, —Br, —I, —CN, —$NO_2$, —CHO, =O, —$R_0$, —$C(=O)R_0$, —$C(=O)H$, —$C(=O)OH$, —$C(=O)OR_0$ and —$OR_0$, wherein N-ring atoms optionally present may in each case be oxidized; where $R_0$ is each independently —$CH_3$, —C(=O)$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2CH(CH_3)_2$, —C($CH_3$)$_3$, —$CH_2CH_2CH_2CH_2CH_3$, —$CH_2CH_2CH_2CH_2CH_2CH_3$, —CH=$CH_2$, —C≡CH, —$CH_2$CH=$CH_2$, —CH=CH—$CH_3$, —$CH_2$C≡CH, —C≡C$CH_3$ and —CH=CHCH=$CH_2$, in each case unsubstituted.

In a further preferred embodiment, X is —$CH_2$— or —S(=O)$_2$—; or is —$CH_2$— or —C(=O)—; or is —S(=O)$_2$— or —C(=O)—; or is —$CH_2$—; or is —S(=O)$_2$—; or is —C(=O)—.

Preferred compounds are
6-methoxy-2-methyl-N-(4-((4-(pyridin-4-ylamino)phenyl)sulfonyl)phenyl)quinolin-4-amine (2)

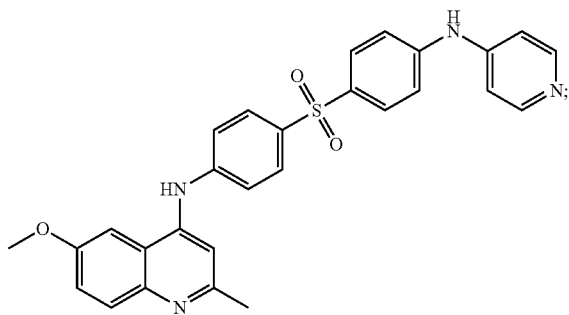 [SMILES: COc1ccc2nc(C)cc(Nc3ccc(S(=O)(=O)c4ccc(Nc5ccncc5)cc4)cc3)c2c1]

and/or
N-(4-(4-aminobenzyl)phenyl)-6-methoxy-2-methylquinolin-4-amine (8)

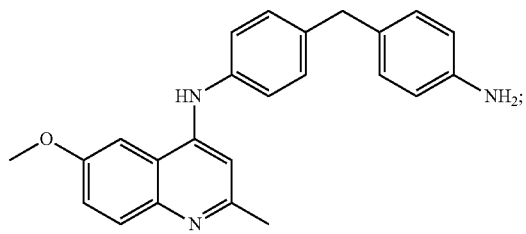 [SMILES: COc1ccc2nc(C)cc(Nc3ccc(Cc4ccc(N)cc4)cc3)c2c1]

and/or
N-(4-((4-aminophenyl)sulfonyl)phenyl)-6-methoxy-2-methylquinolin-4-amine (9)

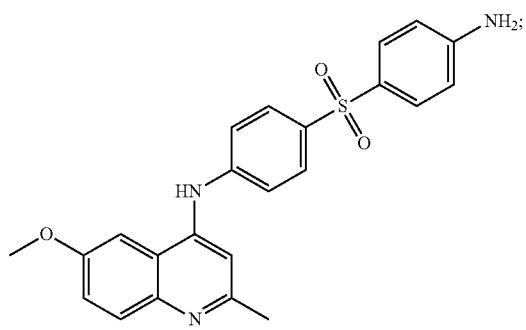 [SMILES: COc1ccc2nc(C)cc(Nc3ccc(S(=O)(=O)c4ccc(N)cc4)cc3)c2c1]

and/or

N-(4-((4-((6-methoxy-2-methylquinolin-4-yl)amino)phenyl)sulfonyl)phenyl)acetamide (10)

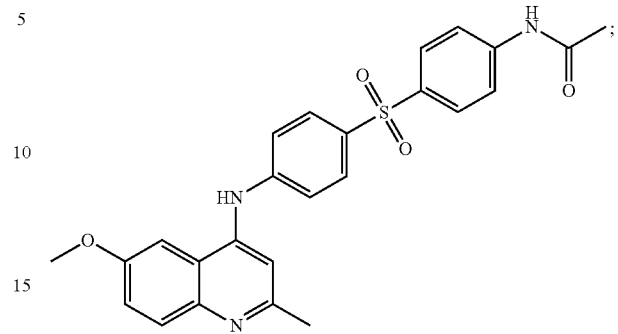

and/or
4-butyl-N-(4-((4-((6-methoxy-2-methylquinolin-4-yl)amino)phenyl)sulfonyl)phenyl)benzamide (11)

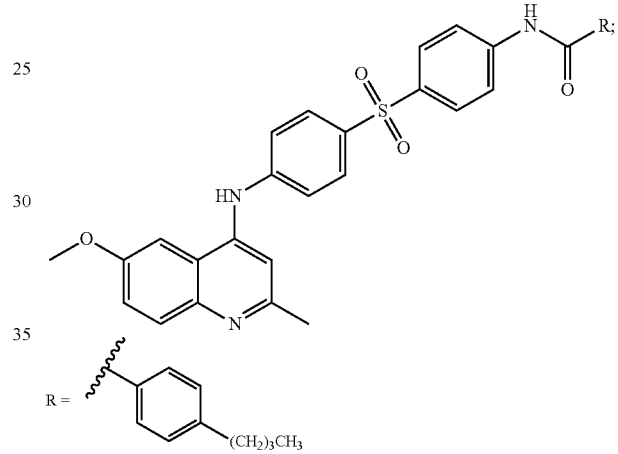

and/or
1-benzyl-3-(tert-butyl)-N-(4-((4-((6-methoxy-2-methylquinolin-4-yl)amino)phenyl)sulfonyl)phenyl)-1H-pyrazole-5-carboxamide (12)

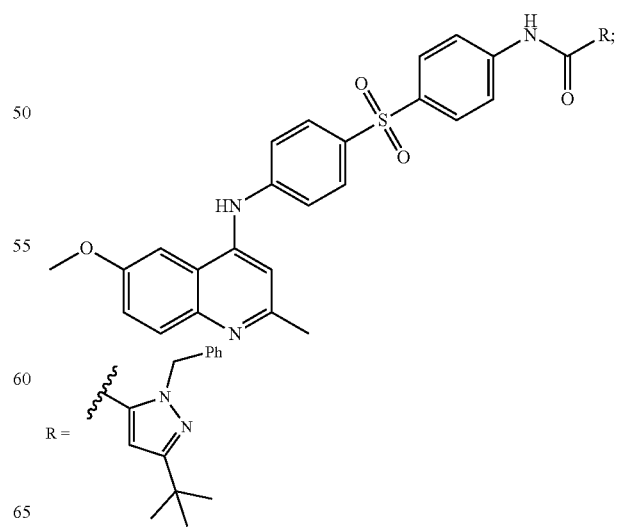

and/or 6-methoxy-2-methyl-N-(4-((4-(pyrimidin-4-yl-amino)phenyl)sulfonyl)phenyl)quinolin-4-amine (24)

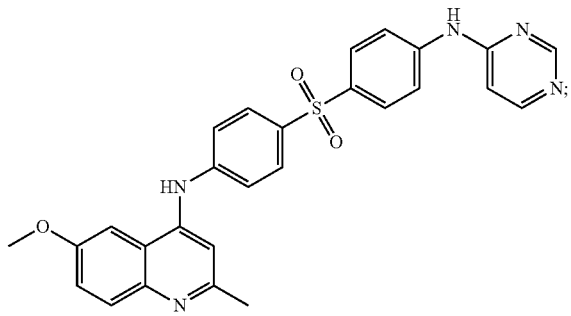 [SMILES: COc1ccc2nc(C)cc(Nc3ccc(S(=O)(=O)c4ccc(Nc5ccncn5)cc4)cc3)c2c1]

and/or

N-(4-((4-((3-(tert-butyl)-1H-pyrazol-5-yl)amino)phenyl)sulfonyl)phenyl)-6methoxy-2-methylquinolin-4-amine (25)

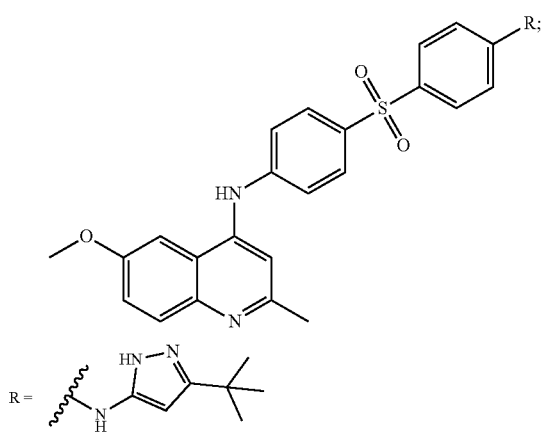

and/or 6-methoxy-N-(4-((4-((4-methoxyphenyl)amino)phenyl)sulfonyl)phenyl)-2-methylquinolin-4-amine (26)

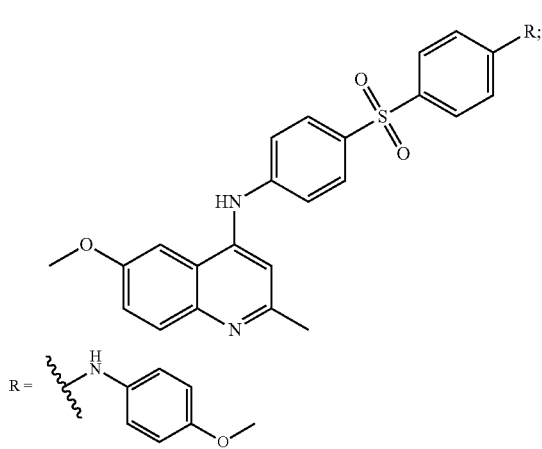

and/or methyl-4-((4-((4-((6-methoxy-2-methylquinolin-4-yl)amino)phenyl)sulfonyl)phenyl)amino) benzoate (27)

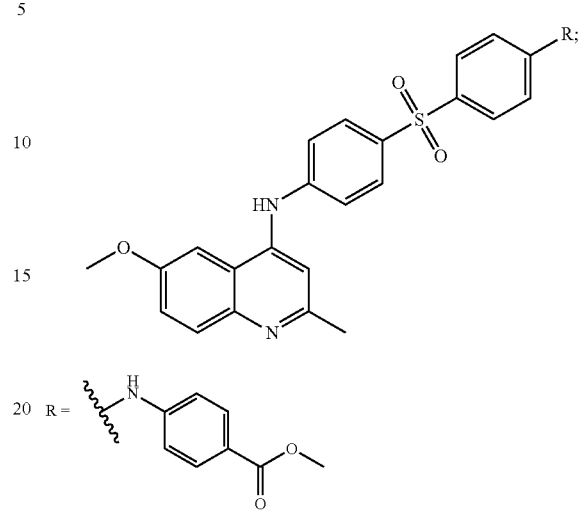

and/or

N-(4-((4-((2-methyl-6-(piperidin-1-yl)quinolin-4-yl)amino)phenyl)sulfonyl)phenyl)acetamide (36)

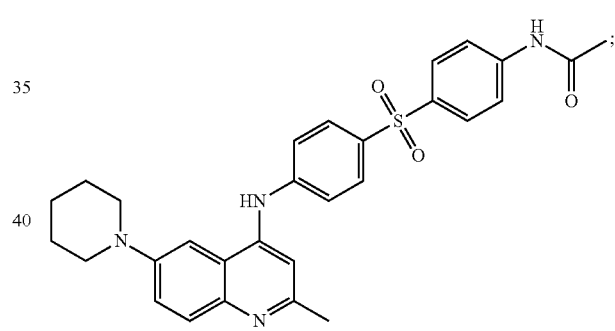

and/or 6-bromo-2-methyl-N-(4-((4-(pyridin-4-yl)amino)phenyl)sulfonyl)phenyl)quinolin-4-amine (37)

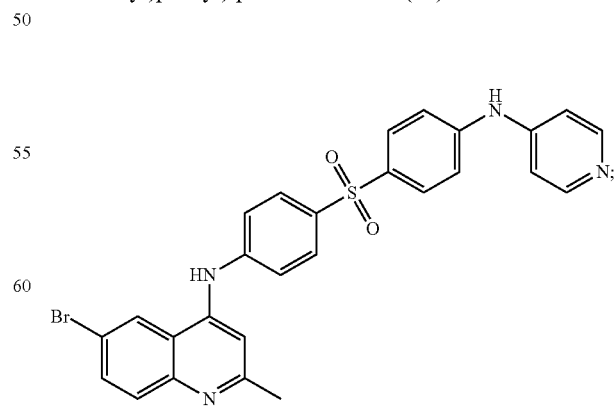

and/or

N-(4-((4-((2-methyl-6-morpholinoquinolin-4-yl)amino)phenyl)sulfonyl)phenyl)acetamide (40)

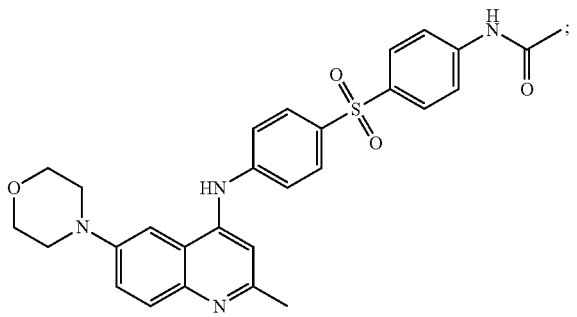 [SMILES: CC(=O)Nc1ccc(S(=O)(=O)c2ccc(Nc3cc(C)nc4ccc(N5CCOCC5)cc34)cc2)cc1]

and/or
(4-((6-methoxy-2-methylquinolin-4-yl)amino)phenyl)(4-(pyridin-4-yl-amino)phenyl)methanone (45)

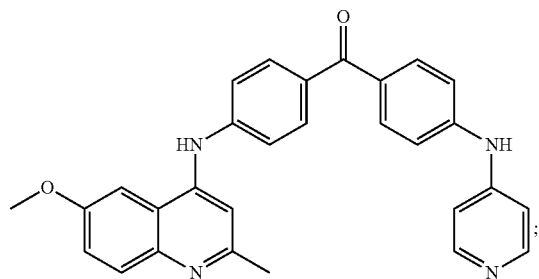 [SMILES: COc1ccc2nc(C)cc(Nc3ccc(C(=O)c4ccc(Nc5ccncc5)cc4)cc3)c2c1]

and/or
(4-((6-methoxy-2-methylquinolin-4-yl)amino)phenyl)(4-(pyrimidin-4-yl-amino)phenyl)methanone (46)

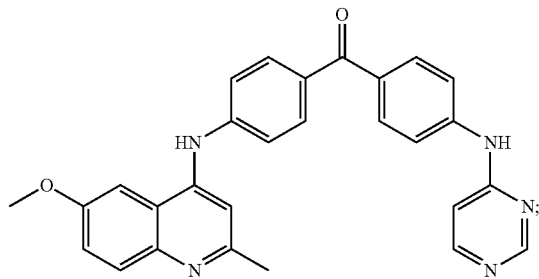 [SMILES: COc1ccc2nc(C)cc(Nc3ccc(C(=O)c4ccc(Nc5ccncn5)cc4)cc3)c2c1]

and/or
6-methoxy-2-methyl-N-(4-(4-(pyridin-4-ylamino)benzyl)phenyl)quinolin-4-amine (63)

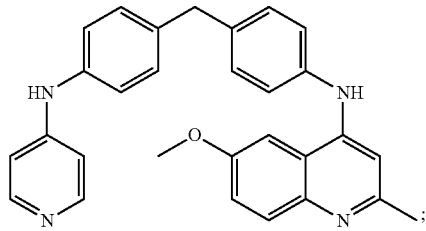 [SMILES: COc1ccc2nc(C)cc(Nc3ccc(Cc4ccc(Nc5ccncc5)cc4)cc3)c2c1]

and/or 6-methoxy-2-methyl-N-(4-(4-(pyrimidin-4-ylamino)benzyl)phenyl)quinolin-4-amine (68)

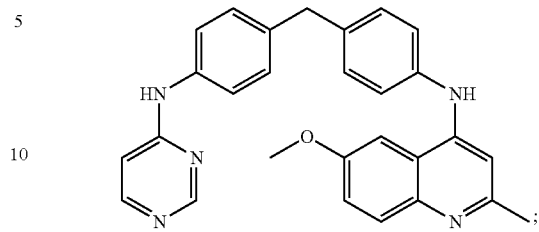

and/or
physiologically acceptable salts thereof.
Particularly preferred compounds are
6-methoxy-2-methyl-N-(4-((4-(pyridin-4-ylamino)phenyl)sulfonyl)phenyl)quinolin-4-amine (2); and/or
N-(4-(4-aminobenzyl)phenyl)-6-methoxy-2-methylquinolin-4-amine (8); and/or
6-methoxy-2-methyl-N-(4-(4-(pyridin-4-ylamino)benzyl)phenyl)quinolin-4-amine (63); and/or
6-methoxy-2-methyl-N-(4-(4-(pyrimidin-4-ylamino)benzyl)phenyl)quinolin-4-amine (68); and/or
physiologically acceptable salts thereof.
Particularly preferred compounds are 6-methoxy-2-methyl-N-(4-(4-(pyrimidin-4-ylamino)benzyl)phenyl)quinolin-4-amine (68) and/or physiologically acceptable salts thereof.

For the purposes of the description, hydrocarbon radicals are divided into aliphatic hydrocarbon radicals on the one hand and aromatic hydrocarbon radicals on the other.

Aliphatic hydrocarbon radicals are in turn subdivided into acyclic aliphatic hydrocarbon radicals on the one hand (="aliphatic") and cyclic aliphatic hydrocarbon radicals, i.e. alicyclic hydrocarbon radicals, on the other hand (="cycloaliphatic"). Cycloaliphatic can be monocyclic or multicyclic. Alicyclic hydrocarbon radicals ("cycloaliphatic") include both pure aliphatic carbocycles and aliphatic heterocycles, i.e.—unless expressly specified—"cycloaliphatic" includes pure aliphatic carbocycles (e.g. cyclohexyl), pure aliphatic heterocycles (e.g. piperidyl or piperazyl), and non-aromatic, multicyclic, optionally mixed systems (e.g. decalinyl, decahydroquinolinyl).

Aromatic hydrocarbons are in turn subdivided into carbocyclic aromatic hydrocarbons on the one hand (="aryl") and heterocyclic aromatic hydrocarbons on the other hand (="heteroaryl").

The assignment of multicyclic, at least partially aromatic systems preferably depends on whether at least one aromatic ring of the multicyclic system has at least one heteroatom (usually N, O or S) in the ring. If at least one such heteroatom is present in this ring, it is preferably a "heteroaryl" (even if a further carbocyclic aromatic or non-aromatic ring with or without heteroatom is optionally present as an additionally present cycle of the multicyclic system); if no such heteroatom is present in any of the optionally two or more aromatic rings of the multicyclic system, it is preferably "aryl" (even if a ring heteroatom is present in an optionally additionally present non-aromatic cycle of the multicyclic system).

Within the cyclic substituents, the following priority accordingly preferably applies to the assignment: heteroaryl>aryl>cycloaliphatic.

For the purposes of the description, monovalent and polyvalent, for example divalent, hydrocarbon radicals are not distinguished conceptually, i.e. "$C_{1-3}$-aliphatic" includes, depending on the context, for example both —$C_{1-3}$-alkyl, —$C_{1-3}$-alkenyl and —$C_{1-3}$-alkynyl, as well as for example —$C_{1-3}$-alkylene-, —$C_{1-3}$-alkenylene- and $C_{1-3}$-alkynylene-.

Aliphatic is preferably in each case a branched or unbranched, saturated or a mono- or polyunsaturated, unsubstituted or mono- or polysubstituted, aliphatic hydrocarbon radical. If aliphatic is mono- or polysubstituted, the substituents are each independently selected from the group consisting of —F, —Cl, —Br, —I, —CN, —$NO_2$, —CHO, =O, —$R_0$, —C(=O)$R_0$, —C(=O)—OH, —C(=O)$OR_0$, —C(=O)$NH_2$, —C(=O)$NHR_0$, —C(=O)N($R_0$)$_2$, —OH, —$OR_0$, —OC(=O)H, —OC(=O)$R_0$, —OC(=O)$OR_0$, —OC(=O)—$NHR_0$, —OC(=O)N($R_0$)$_2$, —SH, —$SR_0$, —$SO_3$H, —S(=O)$_{1-2}$—$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)$OR_0$, —NHC(=O)$NH_2$, —NHC(=O)$NHR_0$, —NH—C(=O)N($R_0$)$_2$, —Si($R_0$)$_3$, —PO($OR_0$)$_2$. Thus, "aliphatic" includes acyclic saturated or unsaturated hydrocarbon radicals which may be branched or straight-chain, i.e. alkanyls, alkenyls and alkynyls. Alkenyls have at least one C=C double bond and alkynyls at least one C≡C triple bond in this case. Preferred unsubstituted monovalent aliphatics include —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2CH(CH_3)_2$, —C($CH_3$)$_3$, —$CH_2CH_2CH_2$—$CH_2CH_3$ and —$CH_2CH_2$—$CH_2CH_2CH_2CH_3$; but also —CH=$CH_2$, —C≡CH, —$CH_2$CH=$CH_2$, —CH=CH—$CH_3$, —$CH_2$C≡CH, —C≡$CCH_3$ and —CH=CHCH=$CH_2$. Preferred unsubstituted divalent aliphatics include —$CH_2$—, —$CH_2CH_2$—, —$CH_2$CH($CH_3$)—, —CH($CH_3$)—$CH_2$—, —$CH_2CH_2CH_2$—, —CH($CH_3$)$CH_2CH_2$—, —$CH_2$CH($CH_3$)—$CH_2$—, —$CH_2CH_2$CH($CH_3$)—, —CH—($CH_2CH_3$)$CH_2$— and —$CH_2CH_2$—$CH_2CH_2$—; but also —CH=CH—, —C≡C—, —$CH_2$CH=CH—, —CH=CHCH$_2$—, —$CH_2$C≡C— and —C≡C—$CH_2$—. Preferred substituted monovalent aliphatics include —$CH_2$F, —$CHF_2$, —$CF_3$, —$CH_2CF_3$, —$CF_2CF_3$, —$CH_2$OH, —$CH_2CH_2$OH, —$CH_2$CHOHCH$_3$, —$CH_2OCH_3$ and $CH_2CH_2OCH_3$. Preferred substituted divalent aliphatics include —$CF_2$—, —$CF_2CF_2$—, —$CH_2$CHOH—, —CHOHCH$_2$— and —$CH_2$CHOHCH$_2$—. Particular preference is given to methyl, ethyl, n-propyl and n-butyl.

Preferably, cycloaliphatic is in each case a saturated or a mono- or polyunsaturated, unsubstituted or mono- or polysubstituted, aliphatic (i.e. non-aromatic), mono- or multicyclic hydrocarbon radical. The number of ring carbon atoms is preferably within the stated range (i.e. a "$C_{3-8}$"-cycloaliphatic preferably has 3, 4, 5, 6, 7 or 8 ring carbon atoms). For the purposes of the description, "$C_{3-8}$-cycloaliphatic" is preferably a cyclic hydrocarbon having 3, 4, 5, 6, 7 or 8 ring carbon atoms, saturated or unsaturated, but not aromatic, with optionally one or two carbon atoms each independently being replaced by an S, N or O heteroatom. If cycloalkyl is mono- or polysubstituted, the substituents are each independently selected from the group consisting of —F, —Cl, —Br, —I, —CN, —$NO_2$, —CHO, =O, —$R_0$, —C(=O)$R_0$, —C(=O)—OH, —C(=O)$OR_0$, —C(=O)$NH_2$, —C(=O)$NHR_0$, —C(=O)N($R_0$)$_2$, —OH, —$OR_0$, —OC(=O)H, —OC(=O)$R_0$, —OC(=O)$OR_0$, —OC(=O)$NHR_0$, —OC(=O)—N($R_0$)$_2$, —SH, —$SR_0$, —$SO_3$H, —S(=O)$_{1-2}$—$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)$OR_0$, —NHC(=O)$NH_2$, —NHC(=O)$NHR_0$, —NH—C(=O)N($R_0$)$_2$, —Si($R_0$)$_3$, —PO($OR_0$)$_2$. Advantageously, $C_{3-8}$-cycloaliphatic is selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

Preferably, in connection with "aliphatic" or "cycloaliphatic", "mono- or polysubstituted" is understood to mean single or multiple substitution, e.g. single, double, triple or quadruple substitution of one or more hydrogen atoms by —F, —Cl, —Br, —I, —OH, —$OC_{1-6}$-alkyl, —OC(=O)$C_{1-6}$-alkyl, —SH, —$NH_2$, —$NHC_{1-6}$-alkyl, —N($C_{1-6}$-alkyl)$_2$, —C(=O)$OC_{1-6}$-alkyl or —C(=O)OH. Preference is given to compounds in which "substituted aliphatic" or "substituted cycloaliphatic" signifies aliphatic or cycloaliphatic substituted by —F, —Cl, —Br, —I, —CN, —$CH_3$, —$C_2H_5$, —$NH_2$, —$NO_2$, —SH, —$CF_3$, —OH, —$OCH_3$, —$OC_2H_5$ or —N($CH_3$)$_2$. Particularly preferred substituents are —F, —Cl, —OH, —SH, —$NH_2$ and —C(=O)OH.

Polysubstituted radicals are to be understood to mean those radicals which are polysubstituted, e.g. di- or trisubstituted, either on different or on the same atoms, for example trisubstituted on the same carbon atom, as in the case of —$CF_3$ or —$CH_2CF_3$, or at different positions, as in the case of —CH(OH)—CH=CH—$CHCl_2$. Multiple substitution can be with the same or different substituents. Optionally, a substituent can also be substituted for its part; for instance, —O aliphatic also includes, inter alia, —$OCH_2CH_2$O—$CH_2CH_2$—OH. It is preferred if aliphatic or cycloaliphatic are substituted by —F, —Cl, —Br, —I, —CN, —$CH_3$, —$C_2H_5$, —$NH_2$, —$NO_2$, —SH, —$CF_3$, —OH, —$OCH_3$, —$OC_2H_5$ or —N($CH_3$)$_2$. It is especially preferred if aliphatic or cycloaliphatic are substituted by —OH, —$OCH_3$ or —$OC_2H_5$.

Preferably, "aryl" is independently in each case a carbocyclic ring system having at least one aromatic ring, but without heteroatoms in said ring, wherein the aryl radicals may optionally be condensed with further saturated, (partially) unsaturated or aromatic ring systems and each aryl radical may be unsubstituted or mono- or polysubstituted, wherein the aryl substituents may be the same or different and in any desired and possible position of the aryl. Preferred aryls are phenyl, naphthyl, anthracenyl, phenanthrenyl, fluoranthenyl, fluorenyl, indanyl and tetralinyl. Particularly preferred are phenyl and naphthyl. Insofar as aryl is mono- or polysubstituted, the aryl substituents may be the same or different and in any desired and possible position of the aryl, and are each independently selected from the group consisting of —F, —Cl, —Br, —I, —CN, —$NO_2$, —CHO, =O, —$R_0$, —C(=O)$R_0$, —C(=O)OH, —C(=O)$OR_0$, —C(=O)—$NH_2$, —C(=O)$NHR_0$, —C(=O)N($R_0$)$_2$, —OH, —O($CH_2$)$_{1-2}$O—, —$OR_0$, —OC(=O)H, —OC(=O)$R_0$, —OC(=O)$OR_0$, —OC(=O)—$NHR_0$, —OC(=O)N($R_0$)$_2$, —SH, —$SR_0$, —$SO_3$H, —S(=O)$_{1-2}$—$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)$OR_0$, —NHC(=O)$NH_2$, —NHC(=O)$NHR_0$, —NH—C(=O)N($R_0$)$_2$, —Si($R_0$)$_3$, —PO($OR_0$)$_2$. Preferred substituted aryls are 2-fluorophenyl, 3-fluorophenyl, 4-fluorophenyl, 2,3-difluorophenyl, 2,4-difluorophenyl, 3,4-difluorophenyl, 2-chlorophenyl, 3-chlorophenyl, 4-chlorophenyl, 2,3-dichlorophenyl, 2,4-dichlorophenyl, 3,4-dichlorophenyl, 2-methoxyphenyl, 3-methoxyphenyl, 4-methoxyphenyl, 2,3-dimethoxyphenyl, 2,4-dimethoxyphenyl, 3,4-dimethoxyphenyl, 2-methylphenyl, 3-methylphenyl, 4-methylphenyl, 2,3-dimethylphenyl, 2,4-dimethylphenyl and 3,4-dimethylphenyl.

Preferably, "heteroaryl" is a 5-, 6- or 7-membered cyclic aromatic radical comprising 1, 2, 3, 4 or 5 heteroatoms, wherein the heteroatoms are the same or different nitrogen, oxygen or sulfur, and the heterocycle may be unsubstituted or mono- or polysubstituted; wherein in the case of substitution on the heterocycle, the substituents may be the same or different and in any desired and possible position of the heteroaryl; and wherein the heterocycle may also be part of a bi- or polycyclic system. Preferably, "heteroaryl" is selected from the group consisting of pyrrolyl, indolyl, furyl (furanyl), benzofuranyl, thienyl (thiophenyl), benzothienyl, benzothiadiazolyl, benzooxadiazolyl, benzothiazolyl, benzooxazolyl, benzotriazolyl, benzodioxolanyl, benzodioxanyl, phthalazinyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the attachment can be via any desired and possible ring member of the heteroaryl radical. Insofar as heteroaryl is mono- or polysubstituted, the heteroaryl substituents can be the same or different and in any desired and possible position of the heteroaryl, and are each independently selected from the group consisting of —F, —Cl, —Br, —I, —CN, —NO$_2$, —CHO, =O, —R$_0$, —C(=O)R$_0$, —C(=O)OH, —C(=O)OR$_0$, —C(=O)—NH$_2$, —C(=O)NHR$_0$, —C(=O)N(R$_0$)$_2$, —OH, —O(CH$_2$)$_{1-2}$O$^-$, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NH—C(=O)R$_0$, —NHC(=O)OR$_0$, —NHC(=O)NH$_2$, —NHC(=O)NHR$_0$, —NH—C(=O)N(R$_0$)$_2$, —Si(R$_0$)$_3$, —PO(OR$_0$)$_2$.

With regard to "aryl" or "heteroaryl", "mono- or polysubstituted" is understood to mean the single or multiple, for example two-, three-, four- or five-fold, substitution of one or more hydrogen atoms of the ring system.

Particularly preferably, the substituents of aryl and heteroaryl are each independently selected from —F, —Cl, —Br, —I, —CN, —CHO, —CO$_2$H, —NH$_2$, —NO$_2$, —NHR$_0$, —N(R$_0$)$_2$, —N$^+$(R$_0$)$_3$, —N$^+$(R$_0$)$_2$O$^-$, —SH, —SR$_0$, —OH, —OR$_0$, —C(=O)R$_0$, —CO$_2$R$_0$, —C(=O)NH$_2$, —C(=O)NHR$_0$, —C(=O)N(R$_0$)$_2$, —S(=O)$_{1-2}$R$_0$, —S(=O)$_2$NH$_2$, —SO$_3$H, =O or —R$_0$. Preferred substituents are —F, —Cl, —Br, —I, —OH, —OC$_{1-6}$-alkyl, —O—C(=O)—C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Preference is given to compounds in which "substituted aryl" or "substituted heteroaryl" signifies aryl or heteroaryl substituted by —F, —Cl, —Br, —I, —CN, —CH$_3$, —C$_2$H5, —NH$_2$, —NO$_2$, —SH, —CF$_3$, —OH, —OCH$_3$, —OC$_2$H$_5$ or —N(CH$_3$)$_2$. Particularly preferred substituents are —F, —Cl, —OH, —SH, —NH$_2$ and —C(=O)OH.

The compounds according to the invention may be in the form of a single stereoisomer or mixture thereof, the free compounds and/or physiologically acceptable salts and/or solvates thereof.

The compounds according to the invention may be chiral or achiral, depending on the substitution pattern.

Depending on the substitution, the compounds according to the invention may be isomers in which the substitution pattern can be referred to as syn/anti. "Syn/anti isomers" are a subset of stereoisomers (configurational isomers).

In a preferred embodiment, the diastereomeric excess of the syn isomer is at least 50% de, preferably at least 75% de, even more preferably at least 90% de, most preferably at least 95% de, and especially at least 99% de. In another preferred embodiment, the diastereomeric excess of the anti isomer is at least 50% de, preferably at least 75% de, even more preferably at least 90% de, most preferably at least 95% de, and especially at least 99% de.

Suitable methods for separating the isomers (diastereomers) are known to those skilled in the art. Column chromatography, preparative HPLC and crystallization methods may be mentioned as examples.

If the compounds according to the invention are chiral, they are preferably present as a racemate or as an enantiomer in an enriched form. In a preferred embodiment, the enantiomeric excess (ee) of the S-enantiomer is at least 50% ee, preferably at least 75% ee, even more preferably at least 90% ee, most preferably at least 95% ee and especially at least 99% ee. In another preferred embodiment, the enantiomeric excess (ee) of the R-enantiomer is at least 50% ee, preferably at least 75% ee, even more preferably at least 90% ee, most preferably at least 95% ee and especially at least 99% ee.

Suitable methods for separating the enantiomers are known to those skilled in the art. Preparative HPLC on chiral stationary phases and conversion to diastereomeric intermediates can be mentioned as examples. The conversion to diastereomeric intermediates can be carried out, for example, by means of salt formation with the aid of chiral, enantiomerically pure acids. After separation of the diastereomers thus formed, the salt can then be converted back again to the free base or another salt.

Unless expressly specified, each reference to the compounds according to the invention includes all isomers (e.g. stereoisomers, diastereomers, enantiomers) in any mixing ratio.

Unless expressly specified, any reference to the compounds according to the invention includes the free compounds (i.e. the forms which are not in the form of a salt) and all physiologically acceptable salts.

For the purposes of the description, physiologically acceptable salts of the compounds according to the invention are present as salts with anions or acids of the respective compound with inorganic or organic acids which are physiologically compatible—especially when used in humans and/or mammals.

Examples of physiologically compatible salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharic acid, monomethylsebacic acid, 5-oxoproline, hexane-1-sulfonic acid, nicotinic acid, 2-, 3- or 4-aminobenzoic acid, 2,4,6-trimethylbenzoic acid, α lipoic acid, acetylglycine, acetylsalicylic acid, hippuric acid and/or aspartic acid. Particularly preferred are the hydrochloride, the citrate and the hemicitrate.

Physiologically acceptable salts with cations or bases are salts of the respective compound—as an anion having at least one, preferably inorganic, cation which are physiologically acceptable—especially when used in humans and/or mammals. Particularly preferred are the salts of alkali metal and alkaline earth metals but also ammonium salts, especially (mono-) or (di)sodium, (mono-) or (di)potassium, magnesium or calcium salts.

In a second aspect, the invention relates to medicaments comprising at least one compound according to the invention or a physiologically acceptable salt thereof, and optionally suitable additives and/or auxiliaries and/or optionally further active ingredients. All preferred embodiments, which have been described above in connection with the compound according to the invention, also correspondingly apply analogously to the medicament according to the invention.

In addition to at least one compound according to the invention, the medicaments according to the invention optionally comprise suitable additives and/or auxiliaries, such as carrier materials, fillers, solvents, diluents, dyes, binders and/or antioxidants. Suitable binders are, for example, syrup acacia, gelatin, sorbitol, tragacanth and polyvinylpyrrolidone. Suitable fillers are, for example, lactose, sugar, corn starch, calcium phosphate, sorbitol and glycine. Suitable antioxidants are, for example, ascorbic acid, butylhydroxyanisole (BHA), butylhydroxytoluene (BHT), salts of ascorbic acid, monothioglycerol, phosphorous acid, vitamin C, vitamin E and derivatives thereof, sodium bisulfite, particularly preferably butylhydroxytoluene or butylhydroxyanisole and α-tocopherol. The suitable additives and/or auxiliaries are preferably used in amounts of 0.01 to 10% by weight, preferably 0.03 to 5% by weight, based on the total weight of the medicament.

The medicaments according to the invention can be administered as liquid dosage forms in the form of injection solutions, drops or juices, as semi-solid dosage forms in the form of granules, tablets, pellets, patches, capsules, patches/spray-on plasters or aerosols. The choice of auxiliaries etc. and the amounts to be used of the same depend on whether the drug is intended to be administered by the oral, peroral, parenteral, intravenous, intraperitoneal, intradermal, intramuscular, intranasal, buccal, rectal or topical routes, for example on the skin, mucous membranes or in the eyes. For oral administration, preparations in the form of tablets, dragees, capsules, granules, drops, juices and syrups are suitable, and for parenteral, topical and inhalative administration, solutions, suspensions, readily reconstitutable dry preparations and sprays are suitable. Compounds according to the invention in a depot, in dissolved form or in a patch, optionally with the addition of agents which promote skin penetration, are suitable percutaneous administration preparations. The compounds according to the invention can be delayed release for preparation forms applicable to oral or percutaneous administration. The compounds according to the invention can also be used in parenteral long-term depot forms such as, for example, implants or implanted pumps. In principle, further active ingredients known to those skilled in the art may be added to the medicaments according to the invention.

The amount of active ingredient to be administered to the patient varies depending on the weight of the patient, the route of administration, the indication and the severity of the disease. Typically, 0.00005 to 50 mg/kg, preferably 0.001 to 0.5 mg/kg of at least one compound according to the invention are administered.

For all of the above forms of the medicaments according to the invention, it is particularly preferred if, in addition to at least one compound according to the invention, the medicament also comprises a further active ingredient, in particular an antibiotic, preferably an antibiotic selected from the group consisting of pyrazinamide, isoniazid, ethambutol, rifampicin, aminoglycosides and fluoroquinolones.

In a preferred form of the medicament, a compound included according to the invention is present as a pure diastereomer and/or enantiomer.

In a third aspect, the invention relates to the compound according to the invention and/or the medicament according to the invention for use as a medicament.

In a fourth aspect, the invention relates to the compound according to the invention and/or the medicament according to the invention for use in the treatment of *tuberculosis*; preferably *tuberculosis* selected from the group consisting of *tuberculosis* of the respiratory organs, *tuberculosis* of the nervous system, *tuberculosis* of other organs, and miliary *tuberculosis*; preferably *tuberculosis* of the respiratory organs selected from the group consisting of pulmonary *tuberculosis*, *tuberculosis* of the intrathoracic lymph nodes, *tuberculosis* of the larynx, trachea and bronchi, and tuberculous pleurisy; and/or *tuberculosis* of the nervous system selected from the group consisting of tuberculous meningitis, and meningeal tuberculoma; and/or *tuberculosis* of other organs selected from the group consisting of *tuberculosis* of the bones and joints, *tuberculosis* of the genitourinary system, *tuberculosis* of peripheral lymph nodes, *tuberculosis* of the intestine, peritoneum and mesenteric lymph nodes, *tuberculosis* of the skin and subcutaneous tissue, *tuberculosis* of the eye, *tuberculosis* of the ear, and *tuberculosis* of the adrenal glands.

The invention relates in a fifth aspect to a method for preparing compounds according to the invention as set forth in the following description and examples.

Preparative Methods

Thin-layer chromatography (TLC): Aluminum TLC films (silica gel 60, fluorescence identifier F264 (60F-254)) from Merck were used. The compounds were detected by UV irradiation at 254 and 360 nm.

Liquid chromatography-mass spectrometry (LC-MS): To record low-resolution mass spectra, a Shimadzu LCMS-8030 was used (column: Luna C18 (2), 100 A, length: 250 mm, internal diameter: 4.6 mm, particle size: 2.5-15 μm, ionization method: electrospray ionization).

High resolution mass spectrometry (HR-MS): To record high-resolution mass spectra, an LTQ orbititrap was used, which was coupled to an Accela HPLC system (column: Hypersil Gold, length: 50 mm, internal diameter: 1 mm, particle size: 1.9 μm, ionization method: electrospray ionization). The wavelength range analyzed was in the range of 200-600 nm. The masses were detected in the m/z range of 150-2000 Th.

Nuclear magnetic resonance spectroscopy (NMR): To characterize the synthesized compounds by $^1$H- and $^{13}$C-NMR, a Varian Mercury 400 (400 MHz), a Bruker Avance DRX 500 (500 MHz) and a Bruker 600 (600 MHz) spectrometer were used. The deuterated solvents used were CDCl$_3$ and DMSO-d$_6$, the detected residual protons of which served as internal reference. The chemical shift δ was specified in ppm and the coupling constant J in Hz. The multiplicity observed with spin-spin coupling was characterized using the following abbreviations: s (singlet), d (doublet), t (triplet), q (quartet), dd (doublet of doublets), m (multiplet).

Column chromatography: The column chromatography stationary phase used was silica gel from VWR with a particle size of 40-63 μm.

Reagents

All solvents used were used as available from the distributor. Unless otherwise stated, other reagents and solvents were used without additional purification.

General Working Procedures

Method A: Amination of 4-chloro-2-methylquinolines. To a solution of 4-chloro-2-methylquinoline (7) and amine in absolute EtOH, a drop of concentrated HCl was added and the reaction mixture was heated under reflux overnight. The reaction was concentrated under reduced pressure and the remaining residue was suspended in DCM and NH$_4$OH and stirred until all the solid had dissolved. The aqueous phase was extracted three times with DCM, the combined organic phases were dried over MgSO$_4$ and concentrated in vacuo. Column chromatography on silica gel (DCM/MeOH) afforded the desired product.

Method B: Synthesis and amide coupling of carbonyl chlorides. To a solution of carboxylic acid (2 equiv.) and catalytic amounts of DMF in DCM was added dropwise oxalyl chloride (2 equiv.) and the reaction stirred for 15 h at RT. The resulting carbonyl chloride was added dropwise at 0° C. to a mixture of N-(4-((4-aminophenyl)sulfonyl)phenyl)-6-methoxy-2-methyl-quinolin-4-amine (9) (1 equiv.) and catalytic amounts of DMAP in pyridine. The reaction mixture was slowly warmed to RT and stirred for a further 4 h. Subsequently, the reaction mixture was concentrated under reduced pressure and the remaining radical was suspended in DCM and saturated NaHCO$_3$ solution. The aqueous phase was extracted three times with DCM, the combined organic phases were dried over MgSO$_4$ and concentrated under reduced pressure. Column chromatography on silica gel (DCM/MeOH) afforded the desired product.

Method C: Buchwald-Hartwig cross-coupling of aryl halides and amines. Into a baked-out Schlenk flask with stirrer bar were weighed aryl halide (1 equiv.), amine (1.2 equiv.), base and Pd catalyst (0.1 equiv.) and ligand (0.1-0.3 equiv.) and the flask sealed with a septum. The flask was evacuated three times with argon, degassed, 1,4-dioxane added, and the septum replaced with a glass stopper. The reaction mixture was then stirred at 100° C. for 24 h. After cooling to RT, the reaction was diluted with DCM, filtered through Celite© and taken up in saturated NaHCO$_3$ solution. The aqueous phase was extracted three times with DCM, the combined organic phases were dried over MgSO$_4$ and the solvent removed under reduced pressure. Column chromatography on silica gel (DCM/MeOH) afforded the desired product.

Synthesis of the Compounds According to the Invention and the Comparative Compound 4-((6-Methoxy-2-methylquinolin-4-yl) amino)phenol (1): 4-Chloro-6-methoxy-2methylquinoline (7) (50 mg, 0.24 mmol, 1 equiv.) and p-aminophenol (39 mg, 0.36 mmol, 1.5 equiv.) were dissolved in absolute EtOH (4 mL) and reacted according to method A to obtain the product as a yellow solid (53 mg, 0.19 mmol, 80%). R$_f$=0.2 (DCM/MeOH, 40:1). LC-MS: m/z=281.38 [M+H]$^+$. HR-MS [M+H]$^+$=calculated 281.12845, found 281.12919 (+2.61325 ppm). $^1$H NMR (DMSO-d$_6$, 500 MHz) δ ppm 9.40 (s, 1H), 8.42 (s, 1H), 7.68 (d, J=2.7 Hz, 1H), 7.65 (d, J=9.1 Hz, 1H), 7.25 (dd, J=9.1, 2.7 Hz, 1H), 7.13 (d, J=8.7 Hz, 2H), 6.85 (d, J=8.7 Hz, 2H), 6.42 (s, 1H), 5.75 (s, 1H), 3.89 (s, 3H), 2.34 (s, 3H). $^{13}$C NMR (DMSO-d$_6$, 126 MHz) δ ppm 155.82, 155.61, 154.53, 148.63, 144.05, 131.37, 129.77, 126.12, 120.47, 118.08, 115.93, 100.87, 100.02, 55.56, 24.80.

6-methoxy-2-methyl-N-(4-((4-(pyridin-4-ylamino)phenyl)sulfonyl)phenyl)quinolin-4-amine (2): N-(4-((4-Bromophenyl)sulfonyl)phenyl)-6-methoxy-2-methylquinolin-4-amine (22) (20 mg, 0.041 mmol, 1 equiv), 4-aminopyridine (5 mg, 0.05 mmol, 1.2 equiv.), NaOtBu (5.5 mg, 0.057 mmol, 1.4 equiv.), Pd$_2$(dba)$_3$ (4 mg, 0.004 mmol, 0.1 equiv.) and triphenylphosphane (2.2 mg, 0.008 mmol, 0.3 equiv.) were reacted according to Method C in 1,4-dioxane (1.5 mL) to give the product as a yellowish solid (10 mg, 0.019 mmol, 48%). R$_f$=0.22 (DCM/MeOH, 10:1). LC-MS: m/z=249.15 [M+H]$^+$. HR-MS [M+H]=calculated 497.16419, found 497.16442 (+0.46338 ppm). $^1$H NMR (DMSO-d$_6$, 500 MHz)) δ ppm 9.35 (s, 1H), 9.26 (s, 1H), 8.29 (dd, J=8.8, 6.3 Hz, 2H), 7.85 (dd, J=8.8, 6.3 Hz, 2H), 7.72-7.78 (m, 2H), 7.55 (d, J=2.7 Hz, 1H), 7.52 (d, J=8.8 Hz, 1H), 7.44 (d, J=8.8 Hz, 1H), 7.32-7.36 (m, 2H), 7.29 (d, J=8.8 Hz, 2H), 7.02-7.08 (m, 2H), 6.62 (d, J=8.8 Hz, 1H), 6.09 (s, 1H), 3.88 (s, 3H), 2.49 (s, 3H). $^{13}$C NMR (DMSO-d$_6$, 126 MHz) δ ppm 156.2, 153.3, 150.3, 150.3, 148.3, 148.1, 145.5, 144.8, 135.0, 133.4, 133.2, 129.0, 128.9, 128.8, 128.3, 126.4, 52.6, 20.7.

6-Methoxy-2-methylquinolin-4(1H)-one (6): To a suspension of 4-p-anisidine (6 g, 40 mmol, 1 equiv.) and ethyl acetoacetate (6.21 mL, 48 mmol, 1.2 equiv.) in toluene (75 mL) was added concentrated AcOH (3 mL). With azeotropic removal of water (Dean-Stark apparatus), the reaction mixture was heated under reflux for 20 h. Subsequently, the solvent was removed under reduced pressure and the resulting solid was suspended in Ph$_2$O (15 mL) and heated to 240° C. for 1 h. The reaction mixture was cooled to 50° C. and warm hexane (50 mL) added. The resulting precipitate was filtered off and washed with copious hexane and acetone to give the product as a white solid (3.5 g, 18 mmol, 46%). $^1$H NMR (DMSO-d$_6$, 500 MHz) δ ppm 11.53 (s, 1H), 7.55-7.37 (m, 2H), 7.24 (dd, J=9.0, 2.9 Hz, 1H), 5.87 (s, 1H), 3.81 (s, 3H), 2.32 (s, 3H). $^{13}$C NMR (DMSO-d$_6$, 126 MHz) δ ppm 176.96, 156.08, 149.41, 135.57, 126.35, 122.52, 120.29, 108.26, 105.21, 56.14, 20.20.

4-Chloro-6-methoxy-2-methylquinoline (7): 6-methoxy-2-methylquinolin-4(1H)-one (6) (3 g, 14 mmol, 1 equiv.) was added portionwise at 0° C. to an excess solution of POCl$_3$ (20 mL). The suspension was then stirred at RT for 30 min and then heated under reflux for 1 h. The excess POCl$_3$ was removed by distillation and the remaining residue was poured slowly onto a mixture of ice and saturated NaHCO$_3$ solution and stirred thoroughly. The pH was adjusted to 9 with NH$_4$OH and the resulting precipitate filtered off to give the product as a reddish solid (3.2 g, 14 mmol, 86%). R$_f$=0.43 (PE/EtOAc, 1:1). LC-MS: m/z=208.6 [M+H]$^+$. 1H NMR (DMSO-d$_6$, 500 MHz) δ ppm 7.87 (d, J=9.1 Hz, 1H), 7.57 (s, 1H), 7.43 (dd, J=9.1, 2.8 Hz, 1H), 7.33 (d, J=2.8 Hz, 1H), 3.91 (s, 3H), 2.59 (s, 3H). $^{13}$C NMR (DMSO-d$_6$, 126 MHz) δ ppm 157.67, 156.07, 144.00, 139.46, 130.42, 124.77, 122.61, 122.04, 101.37, 55.51, 24.12.

N-(4-(4-Aminobenzyl)phenyl)-6-methoxy-2-methylquinolin-4-amine (8): 4-chloro-6-methoxy-2-methylquinoline (7) (50 mg, 0.24 mmol, 1 equiv.) and diaminodiphenylmethane (190 mg, 0.96 mmol, 4 equiv.) were dissolved in absolute EtOH (3 mL) and reacted according to method A to obtain the product as a golden yellow solid (83 mg, 0.2 mmol, 85%). R$_f$=0.3 (DCM/MeOH, 20/1). LC-MS: m/z=370.19 [M+H]$^+$. H NMR (DMSO-d$_6$, 500 MHz) δ ppm 7.82 (d, J=9.1 Hz, 2H), 7.40 (dd, J=9.1, 2.6 Hz, 1H), 7.38-7.28 (m, 4H), 7.01 (d, J=8.3 Hz, 2H), 6.82 (s, 1H), 6.63 (d, J=8.3 Hz, 2H), 5.83 (s, 1H), 3.99 (s, 3H), 3.86 (s, 2H), 2.01 (s, 3H). $^{13}$C NMR (DMSO-d$_6$, 126 MHz) δ ppm 172.02, 155.99, 155.51, 147.89, 146.65, 142.98, 138.12, 138.00, 129.35, 129.14, 128.82, 128.28, 122.91, 121.11, 118.53, 114.09, 113.96, 101.27, 101.09, 55.67, 54.84, 24.14, 21.11.

N-(4-((4-Aminophenyl)sulfonyl)phenyl)-6-methoxy-2-methylquinolin-4-amine (9): 4-chloro-6-methoxy-2methylquinoline (7) (178 mg, 0.86 mmol, 1 equiv.) and diaminodiphenylsulfone (640 mg, 2.5 mmol, 3 equiv.) were dissolved in absolute EtOH (15 mL) and reacted according to method A to obtain the product as a white solid (320 mg, 0.76 mmol, 88%). $R_f$=0.5 (DCM/MeOH, 10:1). LC-MS m/z=420.15 [M+H]$^+$. HRMS [M+H]$^+$=calculated 420.13764, found 420.13755 (−0.21456 ppm). $^1$H NMR (DMSO-d$_6$, 500 MHz) δ ppm 8.62 (s, 1H), 7.36 (d, J=8.8 Hz, 2H), 7.33 (d, J=9.1 Hz, 1H), 7.13 (d, J=8.7 Hz, 3H), 6.99 (d, J=8.8 Hz, 2H), 6.90 (dd, J=9.1, 2.7 Hz, 1H), 6.71 (s, 1H), 6.22 (d, J=8.8 Hz, 2H), 5.68 (s, 2H), 3.45 (s, 3H), 2.75 (s, 3H). $^{13}$C NMR (DMSO-d$_6$, 126 MHz) d$_6$) δ ppm 156.14, 156.07, 153.28, 145.97, 144.56, 144.36, 135.07, 129.91, 129.07, 128.25, 126.50, 121.16, 120.01, 118.77, 112.97, 105.99, 101.17, 55.53, 24.60.

N-(4-((4-((6-methoxy-2-methylquinolin-4-yl)amino)phenyl)sulfonyl)phenyl)acetamide (10): N-(4-((4-aminophenyl)sulfonyl)phenyl)-6-methoxy-2-methylquinolin-4-amine (9) (30 mg, 0.071 mmol, 1 equiv) was dissolved in pyridine (1 mL), Ac$_2$O (0.28 mmol, 40 μL, 4 equiv.) was added and the reaction stirred at RT for 18 h. Subsequently, pyridine was removed under reduced pressure and the residue was taken up in saturated NaHCO$_3$ solution and DCM. The aqueous phase was extracted three times with DCM, the combined organic phases were dried over MgSO$_4$ and concentrated under reduced pressure. Column chromatography on silica gel (DCM/MeOH) afforded the desired product as a white solid (28.5 mg, 0.061 mmol, 87%). $R_f$=0.3 (DCM/MeOH, 10:1). LC-MS: m/z=462.48 [M+H]$^+$. HR-MS [M+H]$^+$=calculated 462.14820, found 462.14815 (−0.11724 ppm). $^1$H NMR (DMSO-d$_6$, 500 MHz) δ ppm 10.36 (s, 1H), 9.12 (s, 1H), 7.92-7.82 (m, 4H), 7.83-7.72 (m, 3H), 7.55 (d, J=2.8 Hz, 1H), 7.49-7.41 (m, 2H), 7.35 (dd, J=9.1, 2.8 Hz, 1H), 7.19 (s, 1H), 3.89 (s, 3H), 2.50 (s, 3H), 2.09 (s, 3H). $^{13}$C NMR (DMSO-d$_6$, 126 MHz) δ ppm 169.01, 156.16, 143.44, 135.43, 132.87, 128.88, 128.23, 121.18, 120.19, 118.91, 118.38, 101.14, 55.50, 24.62, 24.07.

4-Butyl-N-(4-((4-((6-methoxy-2-methylquinolin-4-yl)amino)phenyl)sulfonyl)phenyl)benzamide (11): 4-butylbenzoic acid (25.5 mg, 0.14 mmol, 2 equiv.) was dissolved in DCM (5 mL) and was reacted with N-(4-((4-aminophenyl)sulfonyl)phenyl)-6-methoxy-2-methylquinolin-4-amine (9) (30 mg, 0.071 mmol, 1 equiv.) according to Method B to give the product as a yellow solid (29 mg, 0.05 mmol, 70%). $R_f$=0.55 (DCM/MeOH, 10:1). LC-MS: m/z=580.65 [M+H]$^+$. HR-MS [M+H]$^+$=calculated 580.22645, found 580.22592 (−0.92275 ppm). $^1$H NMR (DMSO-d$_6$, 500 MHz) δ ppm 10.50 (s, 1H), 7.93 (s, 3H), 7.83 (d, J=9.1 Hz, 3H), 7.59 (s, 1H), 7.46 (d, J=7.5 Hz, 2H), 7.37 (d, J=9.1 Hz, 1H), 7.28 (t, J=7.5 Hz, 3H), 7.25-7.14 (m, 2H), 7.14-7.00 (m, 3H), 6.73 (s, 1H), 5.68 (s, 1H), 3.89 (s, 3H), 2.09 (s, 3H), 1.30 (d, J=2.0 Hz, 6H), 1.26 (d, J=2.0 Hz, 3H). $^{13}$C NMR (DMSO-d$_6$, 126 MHz) δ ppm 159.61, 158.33, 156.30, 142.79, 137.98, 136.28, 134.73, 128.95, 128.31, 128.13, 127.19, 127.13, 126.86, 126.68, 121.53, 120.32, 120.04, 118.89, 107.41, 105.35, 101.31, 55.57, 53.73, 53.59, 31.74, 31.65, 30.29, 30.22.

1-Benzyl-3-(tert-butyl)-N-(4-((4-((6-methoxy-2-methylquinolin-4-yl)amino)phenyl)sulfonyl)phenyl)-1H-pyrazole-5-carboxamide (12): 1-benzyl-3-tert-butyl-1H-pyrrazole-5-carboxylic acid (36 mg, 0.14 mmol, 2 equiv.) was dissolved in DCM (5 mL) and reacted with N-(4-((4-aminophenyl)sulfonyl)phenyl)-6-methoxy-2-methylquinolin-4-amine (9) (30 mg, 0.071 mmol, 1 equiv.) according to method B to give the product as a yellow solid (31 mg, 0.047 mmol, 67%). $R_f$=0.5 (DCM/MeOH, 10:1). LC-MS: m/z=660.25 [M+H]$^+$. HR-MS [M+H]$^+$=calculated 660.26390, found 660.26466 (+1.14775 ppm). $^1$H NMR (DMSO-d$_6$, 500 MHz) δ ppm 10.51 (br. s., 1H), 9.49 (br. s., 1H) 9.29-9.67 (m, 1H), 7.94 (br. s., 4H), 7.58-7.84 (m, 2H), 7.33-7.58 (m, 2H), 6.92-7.34 (m, 7H), 5.68 (br. s., 2H), 3.90 (s., 3H), 2.43 (s, 3H), 1.29 (br. s., 9H). $^{13}$C NMR (DMSO-d$_6$, 126 MHz) δ ppm 183.1, 165.2, 155.6, 153.2, 151.0, 150.3, 146.0, 145.6, 142.4, 141.1, 138.0, 136.3, 133.7, 131.8, 130.6, 128.3, 128.2, 126.9, 126.8, 124.1, 120.4, 116.2, 114.8, 114.3, 107.9, 105.4, 101.5, 57.8, 55.7, 51.9, 30.3, 27.4, 24.3.

1-Bromo-4-((4-nitrophenyl)sulfonyl)benzene (18): 4-nitrobenzenesulfonyl chloride (3.58 g, 16.2 mmol, 1 equiv.) and AlCl$_3$ (3.23 g, 24.2 mmol, 1.5 equiv.) was dissolved in bromobenzene (4.23 mL, 40.4 mmol, 2.5 equiv.) and stirred for 30 minutes at RT. Subsequently, the reaction mixture was gradually heated to 100° C. over 1.5 h and stirred for a further 4 h. After cooling to RT, the reaction was precipitated on ice water, the resulting solid was filtered off and washed with water and iPrOH. The crude product was then recrystallized from EtOH/EtOAc to give the product as yellow-brown solid (4 g, 11.7 mmol, 72%). $R_f$=0.87 (PE/EA, 1:1). LC-MS: m/z=365.35 [M+Na]$^+$. $^1$H NMR (DMSO-d$_6$, 500 MHz) δ ppm 8.40 (d, J=5.0 Hz, 2H), 8.24 (d, J=5.0 Hz, 2H), 7.95 (d, J=5.0 Hz, 2H), 7.88 (J=5.0 Hz, 2H). $^{13}$C NMR (DMSO-d6, 126 MHz) δ ppm 176.04, 155.15, 148.48, 134.64, 125.43, 121.59, 119.36, 107.33, 104.28.

N-(4-((4-Aminophenyl)sulfonyl)phenyl) pyridin-4-amine (20): N-(4-((4-nitrophenyl)sulfonyl)phenyl)pyridin-4-amine (64 mg, 0.18 mmol, 1 equiv.) was dissolved in EtOH/H$_2$O (3:1 mL) and Na$_2$S$_2$O$_4$ (184 mg, 0.9 mmol, 5 equiv.) was added and the reaction mixture was stirred at 75° C. for 30 h. After cooling to RT, the reaction was concentrated under reduced pressure, DCM and saturated NaHCO$_3$ solution were added, and the pH was adjusted to 9 with NH$_4$OH. The aqueous phase was extracted three times with DCM and the combined organic phases were dried over MgSO$_4$. Column chromatography on silica gel (DCM/MeOH) afforded the desired product as a white solid (45 mg, 0.13 mmol, 76%). $R_f$=0.18 (DCM/MeOH, 10:1). LC-MS: m/z=326.4 [M+H]$^+$. $^1$H NMR (DMSO-d$_6$, 400 MHz) δ ppm 9.31 (s, 1H), 8.28 (d, J=8.5 Hz, 2H), 7.74 (d, J=8.5 Hz, 2H), 7.52 (d, J=8.5 Hz, 2H), 7.29 (d, J=8.5 Hz, 2H), 7.03-7.05 (d, J=8.5 Hz, 2H), 6.61 (d, J=8.5 Hz, 2H), 6.12 (s, 2H). $^{13}$C NMR (DMSO-d$_6$, 101 MHz) δ ppm 153.3, 150.3, 148.3, 144.9, 135.0, 129.1, 128.3, 126.4, 117.8, 113.0, 110.9.

4-((4-Bromophenyl)sulfonyl)aniline (21): 1-bromo-4-((4-nitrophenyl)sulfonyl)benzene (18) (310 mg, 0.91 mmol, 1 equiv) was dissolved in EtOH/DMSO (4:1 mL), Na$_2$S$_2$O$_4$ (937.2 mg, 4.55 mmol, 5 equiv.) was added and the reaction mixture stirred at 85° C. for 30 h. After cooling to RT, the reaction was concentrated under reduced pressure, EtOAc and saturated NaHCO$_3$ solution were added, and the pH was adjusted to 9 with NH$_4$OH. The aqueous phase was extracted three times with EtOAc and the combined organic phases were dried over MgSO$_4$. Column chromatography on silica gel (PE/EA) afforded the desired product as a brown solid (140 mg, 0.44 mmol, 50%). $R_f$=0.87 (PE/EA, 1:1). $^1$H NMR (MeOH-d4, 400 MHz): δ ppm 5.95-5.99 (m, 2H), 5.84-5.92 (m, 4H), 5.67 (br. s, 2H), 4.97-5.02 (m, 2H). $^{13}$C NMR (MeOH-d4, 101 MHz): δ ppm 206.2, 123.2, 120.5, 119.3, 105.6, 68.1.

N-(4-((4-Bromophenyl)sulfonyl)phenyl)-6-methoxy-2-methylquinolin-4-amine (22): 4-chloro-6-methoxy-2-methylquinoline (7) (100 mg, 0.47 mmol, 1.1 equiv.) and 4-((4-bromophenyl)sulfonyl)aniline (21) (135 mg, 0.43 mmol, 1 equiv.) were dissolved in absolute EtOH (6 mL), 1 drop of concentrated HCl was added and reacted according to Method A to give the product as an orange solid (190 mg, 0.39 mmol, 89%). $R_f$=0.26 (PE/EA, 1:1). LC-MS: m/z=482.95 [M+H]$^+$. $^1$H NMR (DMSO-d$_6$, 400 MHz) δ ppm 9.19 (s, 1H), 7.82-7.91 (m, 6H), 7.78 (d, J=9.0 Hz, 1H), 7.52 (d, J=2.8 Hz, 1H), 7.44 (d, J=9.0 Hz, 2H), 7.34 (dd, J=9.0, 2.8 Hz, 1H), 7.21 (s, 1H), 3.87 (s, 3H), 2.49 (s, 3H). $^{13}$C NMR (DMSO-$d_6$, 101 MHz) δ ppm 156.2, 147.5, 144.6, 143.9, 141.4, 132.8, 131.3, 130.2, 129.4, 129.0, 127.3, 121.3, 120.4, 118.2, 107.3, 101.1, 59.8, 55.6, 24.7.

6-Methoxy-2-methyl-N-(4-((4-(pyrimidin-4-yl-amino)phenyl)sulfonyl)phenyl)quinolin-4-amine (24): N-(4-((4-bromophenyl)sulfonyl)phenyl)-6-methoxy-2-methylquinolin-4-amine (22) (30 mg, 0.062 mmol, 1 equiv.), 4-aminopyrimidine (7 mg, 0.074 mmol, 1.2 equiv.), NaOtBu (8.5 mg, 0.087 mmol, 1.4 equiv.), Pd$_2$(dba)$_3$ (6 mg, 0.006 mmol, 0.1 equiv.) and triphenylphosphane (2.2 mg, 0.018 mmol, 0.3 equiv.) were reacted according to Method C in 1,4-dioxane (2 mL) to give the product as a white solid (13.25 mg, 0.027 mmol, 43.5%). $R_f$=0.37 (DCM/MeOH, 10:1). LC-MS: m/z=498.2 [M+H]$^+$. HR-MS [M+H]$^+$=calculated 498.15944, found 498.15956 (+0.24720 ppm). $^1$H NMR (DMSO-$d_6$, 500 MHz) δ ppm 10.18 (br. s., 1H), 9.15 (br. s., 1H), 8.71 (s, 1H), 8.29-8.39 (m, 2H), 8.02 (d, J=6.5 Hz, 1H), 7.93-7.99 (m, 2H), 7.83-7.92 (m, 4H), 7.76 (d, J=9.2 Hz, 1H), 7.56 (d, J=2.3 Hz, 1H), 7.45 (d, J=9.2 Hz, 2H), 7.33 (dd, J=9.2, 2.7 Hz, 1H), 7.18 (s, 1H), 6.92 (d, J=6.5 Hz, 1H), 6.78 (br. s., 1H), 6.40 (d, J=7.3 Hz, 1H), 3.87 (s, 3H), 2.48 (s, 3H). $^{13}$C NMR (DMSO-$d_6$, 126 MHz) δ ppm 158.1, 157.6, 155.9, 155.6, 154.5, 146.6, 144.4, 144.1, 143.9, 134.0, 132.9, 129.9, 128.6, 128.1, 121.0, 120.0, 118.9, 118.2, 108.2, 104.8, 101.0, 55.3, 24.5.

N-(4-((4-((3-(tert-butyl)-1H-pyrazol-5-yl)amino)phenyl)sulfonyl)phenyl)-6methoxy-2-methylquinolin-4-amine (25): N-(4-((4-bromophenyl)sulfonyl)phenyl)-6-methoxy-2-methyl-quinolin-4-amine (22) (35 mg, 0.072 mmol, 1 equiv), 3-(tert-butyl)-1H-pyrazol-5-amine (11 mg, 0.081 mmol, 1.2 equiv.), NaOtBu (10.5 mg, 0.1 mmol, 1.4 equiv.) and PdCl$_2$ (dppf)(6 mg, 0.007 mmol, 0.1 equiv.) were reacted according to Method C in 1,4-dioxane (1.5 mL) to give the product as a dark brown solid (10 mg, 0.018 mmol, 26%). $R_f$=0.24 (DCM/MeOH, 10:1). LC-MS: m/z=542.55 [M+H]$^+$. HR-MS [M+H]$^+$=calculated 542.22204, found 542.22205 (+0.03003 ppm). $^1$H NMR (DMSO-$d_6$, 500 MHz) δ ppm 12.63 (br. s., 1H), 11.92 (br. s., 1H), 9.04 (d, J=8.8 Hz, 2H), 7.81 (d, J=8.8 Hz, 2H), 7.76 (d, J=8.8 Hz, 1H), 7.70 (d, J=8.8 Hz, 1H), 7.55 (d, J=2.7 Hz, 1H), 7.39-7.47 (m, 2H), 7.33 (dd, J=8.8, 2.7 Hz, 2H), 7.16 (s, H), 3.87 (s, 3H), 1.26 (s, 3H), 1.18 (s, 9H). $^{13}$C NMR (DMSO-$d_6$, 126 MHz) δ ppm 155.7, 154.3, 152.6, 131.4, 129.8, 128.3, 128.1, 125.7, 123.9, 120.8, 119.7, 118.2, 113.8, 93.1, 65.9, 55.2, 30.3, 29.7, 29.5, 24.3.

6-Methoxy-N-(4-((4-((4-methoxyphenyl)amino)phenyl)sulfonyl)phenyl)-2-methylquinolin-4-amine (26): N-(4-((4-bromophenyl)sulfonyl)phenyl)-6-methoxy-2-methylquinolin-4-amine (22) (30 mg, 0.062 mmol, 1 equiv), p-anisidine (9.15 mg, 0.074 mmol, 1.2 equiv.), NaOtBu (8.5 mg, 0.087 mmol, 1.4 equiv.), Pd$_2$(dba)$_3$ (6 mg, 0.006 mmol, 0.1 equiv.) and triphenylphosphane (3.3 mg, 0.018 mmol, 0.3 equiv.) were reacted according to Method C in 1,4-dioxane (2 mL) to give the product as a pale brown solid (24.8 mg, 0.047 mmol, 76%). $R_f$=0.49 (DCM/MeOH, 10:1). LC-MS: m/z=526.25 [M+H]$^+$. HR-MS [M+H]$^+$=calculated 526.1795, found 526.17966 (+0.30337 ppm). $^1$H NMR (DMSO-$d_6$, 500 MHz) δ ppm 9.09 (br. s., 1H), 8.62 (s, 1H), 7.81 (d, J=8.8 Hz, 2H), 7.77 (d, J=9.2 Hz, 2H), 7.67 (d, J=9.2 Hz, 2H), 7.57 (d, J=2.3 Hz, 1H), 7.43 (d, J=8.8 Hz, 2H), 7.34 (dd, J=9.2, 2.7 Hz, 1H), 7.15 (s, 1H), 7.12 (d, J=8.8 Hz, 2H), 6.93 (dd, J=9.2, 2.7 Hz, 4H), 3.88 (s, 3H), 3.74 (s, 3H), 2.49 (s, 3H). $^{13}$C NMR (DMSO-$d_6$, 126 MHz): δ ppm 156.0, 150.2, 146.3, 134.1, 129.2, 128.9, 128.6, 123.5, 121.4, 120.2, 118.9, 114.8, 113.1, 101.3, 66.5, 55.7, 55.4, 24.7

Methyl-4-((4-((4-((6-methoxy-2-methylquinolin-4-yl)amino)phenyl)sulfonyl)phenyl)amino) benzoate (27): N-(4-((4-bromophenyl)sulfonyl)phenyl)-6-methoxy-2-methylquinolin-4-amine (22) (30 mg, 0.062 mmol, 1 equiv), methyl 4-aminobenzoate (11 mg, 0.074 mmol, 1.2 equiv.), NaOtBu (8.5 mg, 0.087 mmol, 1.4 equiv.), Pd$_2$(dba)$_3$ (6 mg, 0.006 mmol, 0.1 equiv.) and triphenylphosphane (3.3 mg, 0.018 mmol, 0.3 equiv.) were reacted according to Method C in 1,4-dioxane (2 mL) to give the product as a golden yellow solid (21.5 mg, 0.039 mmol, 64%). $R_f$=0.45 (DCM/MeOH, 10:1). LC-MS: m/z=554.4 [M+H]$^+$. HR-MS [M+H]$^+$=calculated 554.17442, found 554.17486 (+0.79483 ppm). $^1$H NMR (DMSO-$d_6$, 500 MHz) δ ppm 9.33 (s, 1H), 9.13 (br. s., 1H), 7.87 (dd, J=9.2, 8.8 Hz, 4H), 7.82 (d, J=9.2 Hz, 2H), 7.77 (d, J=9.2 Hz, 1H), 7.56 (d, J=2.7 Hz, 1H), 7.45 (d, J=8.8 Hz, 2H), 7.35 (dd, J=9.2, 2.7 Hz, 1H), 7.29 (d, J=8.8 Hz, 2H), 7.23 (d, J=8.8 Hz, 2H), 7.17 (s, 1H), 3.88 (s, 3H), 3.81 (s, 3H), 2.49 (s., 3H). $^{13}$C NMR (DMSO-$d_6$, 126 MHz δ ppm 165.8, 156.2, 146.4, 146.0, 132.4, 130.9, 128.9, 128.7, 121.6, 121.2, 118.6, 116.7, 116.7, 101.2, 66.3, 59.7, 55.5, 51.6, 24.5, 20.7.

6-Bromo-2-methylquinolin-4(1H)-one (31): To a suspension of 4-bromoaniline (6.88 g, 40 mmol, 1 equiv.) and ethyl acetoacetate (6.63 mL, 52 mmol, 1.3 equiv.) in toluene (75 mL) was added concentrated AcOH (3 mL). With azeotropic removal of water (Dean-Stark apparatus), the reaction mixture was heated under reflux for 2 h. Subsequently, the solvent was removed under reduced pressure and the resulting solid was suspended in Ph$_2$O (15 mL) and heated to 240° C. for 1.5 h. The reaction mixture was cooled to 50° C. and warm hexane (50 mL) added. The resulting precipitate was filtered off and washed with copious hexane and acetone to give the product as a white solid (2.26 g, 11.2 mmol, 28%). LC-MS: m/z=238.4 [M+H]$^+$. H NMR (DMSO-$d_6$, 500 MHz) δ ppm 11.69 (s, 1H), 8.10 (d, J=2.3 Hz, 1H), 7.74 (dd, J=8.8, 2.3 Hz, 1H), 7.46 (d, J=8.8 Hz, 1H), 5.95 (s, 1H), 2.33 (s, 3H). $^{13}$C NMR (DMSO-$d_6$, 126 MHz) δ ppm 175.29, 150.18, 138.92, 134.08, 126.92, 125.91, 120.33, 115.24, 108.65, 19.43.

6-Bromo-4-chloro-2-methylquinoline (32): 6-methoxy-2-methylquinolin-4(1H)-one (31) (1.38 g, 5.46 mmol, 1 equiv.) was added portionwise at 0° C. to an excess solution of POCl$_3$ (8 mL). The suspension was then stirred at RT for 30 min and then heated under reflux for 1.5 h. The excess POCl$_3$ was removed by distillation and the remaining radical was poured slowly onto a mixture of ice and saturated NaHCO$_3$ solution and stirred thoroughly. The pH was adjusted to 9 with NH$_4$OH and the resulting precipitate filtered off to give the product as a reddish solid (1.2 g, 4.69 mmol, 85%). $R_f$=0.62 (PE/EA, 2:1). LC-MS: m/z=256.25 [M+H]+. $^1$H NMR (CDCl$_3$, 400 MHz) δ ppm 8.31 (d, J=2.0 Hz, 1H), 7.91 (d, J=8.9 Hz, 1H), 7.79 (dd, J=8.9, 2.0 Hz, 1H), 7.40 (s, 1H), 2.71 (s, 3H). $^{13}$C NMR (CDCl$_3$, 101 MHz) δ ppm 159.40, 146.93, 141.84, 134.17, 130.53, 126.39, 122.85, 121.09, 25.13.

N-(4-((4-Aminophenyl)sulfonyl)phenyl)acetamide (34): To a solution of 4,4'-sulfonyldianiline (283 mg, 1.1 mmol, 3 equiv.) in pyridine (1 mL) was added Ac$_2$O (36 μL, 0.38 mmol, 1 equiv.) and catalytic amounts of DMAP and the reaction stirred for 10 h at RT. Column chromatography on silica gel (DCM/MeOH) afforded the desired product as a white solid (100 mg, 0.034 mmol, 88%). $R_f$=0.51 (DCM/MeOH, 10:1). LC-MS: m/z=291.05 [M+H]$^+$. $^1$H NMR (DMSO-$d_6$, 400 MHz) δ ppm 10.31 (s, 1H), 7.70-7.77 (m, 2H), 7.50 (d, J=8.8 Hz, 2H), 6.60 (d, J=8.8 Hz, 2H), 6.13 (s, 2H), 2.06 (s, 3H). $^{13}$C NMR (DMSO-d$_6$, 101 MHz) δ ppm 169.0, 153.4, 142.9, 136.8, 129.2, 127.7, 126.1, 118.8, 112.9, 24.1, 22.8.

N-(4-((4-((6-bromo-2-methylquinolin-4-yl)amino)phenyl)sulfonyl)phenyl)acetamide (35): 4-chloro-6-methoxy-2-methylquinoline (7) (95.7 mg, 0.37 mmol, 1.1 equiv.) and N-(4-((4-aminophenyl)sulfonyl)phenylacetamide (34) (10 mg, 0.34 mmol, 1 equiv.) were dissolved in absolute EtOH (5 mL), one drop of concentrated HCl was added and reacted according to Method A to give the product as a green solid (65 mg, 0.12 mmol, 37%). $R_f$=0.45 (DCM/MeOH, 10:1). $^1$H NMR (DMSO-d$_6$, 400 MHz) δ ppm 10.38 (s, 1H), 9.34 (s, 1H), 8.48 (s, 1H), 7.82-7.92 (m, 4H), 7.73-7.83 (m, 4H), 7.48 (d, J=8.8 Hz, 1H), 7.24 (s, 5H), 5.76 (s, 1H), 2.78 (s, 3H) 2.07 (s, 3H). $^{13}$C NMR (DMSO-d$_6$, 101 MHz) δ ppm 168.9, 135.1, 132.3, 130.6, 128.7, 128.2, 124.3, 118.8, 54.7, 24.0, 22.1.

N-(4-((4-((2-methyl-6-(piperidin-1-yl)quinolin-4-yl) amino)phenyl)sulfonyl)phenyl)acetamide (36): (a) N-(4-((4-((6-bromo-2-methylquinolin-4-yl)amino)phenyl)sulfonyl) phenyl)acetamide (35) (60 mg, 0.12 mmol, 1 equiv.), piperidine (14 μL, 0.14 mmol, 1.2 equiv.), NaOtBu (16 mg, 0.16 mmol, 1.4 equiv.) and PdCl$_2$ (dppf)(8 mg, 0.01 mmol, 0.1 equiv.) were reacted according to Method C in 1,4-dioxane (2.5 mL) to give the product as a yellow solid (5 mg, 0.095 mmol, 7.5%). (b) To a solution of N-(4-((4-aminophenyl)sulfonyl)phenyl)-2-methyl-6-(piperidin-1-yl)quinolin-4-amine (38) (12 mg, 0.025 mmol, 1 equiv.) in pyridine (0.5 mL) was added Ac$_2$O (24 μL, 0.126 mmol, 10 equiv.) and catalytic amounts of DMAP and the mixture stirred for 22 h at RT. Subsequently, column chromatography on silica gel (DCM/MeOH) afforded the desired product as a yellow solid (10 mg, 0.019 mmol, 76%). $R_f$=0.4 (DCM/MeOH, 10:1). LC-MS: m/z=515.3 [M+H]$^+$. HR-MS [M+H]$^+$=calculated 515.21114, found 515.21109 (−0.09038 ppm). $^1$H NMR (DMSO-d$_6$, 500 MHz) δ ppm 10.41 (s, 1H), 10.40 (br. s., 1H), 7.81-7.89 (m, 4H), 7.77-7.81 (m, 2H), 7.69 (d, J=9.2 Hz, 1H), 7.51 (dd, J=9.4, 2.5 Hz, 1H), 7.40 (d, J=8.4 Hz, 1H), 7.31-7.36 (m, 1H), 7.09 (s, 1H), 3.20-3.26 (m, 2H), 2.08 (s, 3H), 1.91 (s, 3H), 1.49-1.68 ppm (m, 4H). $^{13}$C NMR (DMSO-d$_6$, 126 MHz) δ ppm 172.1, 161.0, 153.8, 150.9, 148.1, 143.7, 140.7, 131.9, 129.0, 128.4, 120.7, 119.1, 113.5, 109.8, 106.3, 101.2, 56.9, 25.4, 24.3, 21.2.

6-Bromo-2-methyl-N-(4-((4-(pyridin-4-ylamino)phenyl) sulfonyl)phenyl)quinolin-4-amine (37): 6-bromo-4-chloro-2-methylquinoline (32) (17.4 mg, 0.067 mmol, 1.1 equiv.) and N-(4-((4-aminophenyl)sulfonyl)phenyl)pyridin-4amine (20) (20 mg, 0.062 mmol, 1 equiv.) were dissolved in absolute EtOH (2 mL), one drop of concentrated HCl was added and reacted according to Method A to give the product as a yellow solid (30.5 mg, 0.055 mmol, 87%). $R_f$=0.18 (DCM/MeOH, 10:1). LC-MS: m/z=547.2 [M+H]$^+$. H NMR (DMSO-d$_6$, 400 MHz) δ ppm 9.39 (s, 1H), 8.49 (d, J=1.8 Hz, 1H), 8.31 (br. s., 2H), 7.87 (t, J=8.5 Hz, 2H), 7.75-7.81 (m, 2H), 7.49 (d, J=9.0 Hz, 2H), 7.35 (d, J=9.0 Hz, 2H), 7.24 (br. s., 1H), 7.07 (d, J=5.3 Hz, 2H), 2.50 (s, 3H). $^{13}$C NMR (DMSO-d$_6$, 101 MHz) δ ppm 150.2, 147.9, 145.4, 133.8, 133.0, 132.3, 130.6, 128.8, 128.6, 124.3, 119.0, 117.5, 111.0, 105.9, 24.8.

N-(4-((4-aminophenyl)sulfonyl)phenyl)-2-methyl-6-(piperidin-1-yl)quinolin-4-amine (38): 6-Bromo-4-chloro-2-methylquinoline (32) (100 mg, 0.39 mmol, 1 equiv), piperidine (38.7 μL, 0.39 mmol, 1 equiv.), Cs$_2$CO$_3$ (317 mg, 0.98 mmol, 2.5 equiv.), Pd$_2$(dba)$_3$ (40 mg, 0.04 mmol, 0.1 equiv.) and triphenylphosphane (21 mg, 0.12 mmol, 0.3 Equiv.) were reacted according to method C in 1,4-dioxane (3 mL), wherein after filtering off the catalyst over Celite©, the crude product was concentrated under reduced pressure and then dissolved in 3 mL of absolute EtOH, whereupon 4,4'-sulfonyldianiline (290 mg, 1.17 mmol, 3 equiv.) and one drop of concentrated HCl were added and the reaction according to method A was further reacted. The product was obtained as a yellow solid (18 mg, 0.038 mmol, 10%). $R_f$=0.35 (DCM/MeOH, 10:1). LC-MS: m/z=473.15 [M+H]$^+$. $^1$H NMR (DMSO-d$_6$, 500 MHz) δ ppm 9.33 (s, 1H), 7.74-7.83 (m, 4H), 7.69 (d, J=8.8 Hz, 2H), 7.54 (d, J=8.8 Hz, 4H), 7.37-7.43 (m, 4H), 7.05 (s, 1H), 6.60-6.67 (m, 4H), 6.12 (s, 2H), 5.75 (s, 1H), 3.22-3.28 (m, 2H), 2.47 (s, 3H), 1.49-1.70 (m, 6H). $^{13}$C NMR (DMSO-d$_6$, 126 MHz) δ ppm 159.9, 149.0, 147.9, 144.0, 139.1, 129.4, 128.5, 126.7, 125.5, 124.6, 122.6, 119.7, 117.0, 113.3, 50.0, 25.5, 24.2, 19.9.

N-(4-((4-Aminophenyl)sulfonyl)phenyl)-2-methyl-6-morpholinoquinolin-4-amine (39): 6-Bromo-4-chloro-2-methylquinoline (32) (100 mg, 0.39 mmol, 1 equiv), morpholine (34 μL, 0.39 mmol, 1 equiv.), Cs$_2$CO$_3$ (317 mg, 0.98 mmol, 2.5 equiv.), Pd$_2$(dba)$_3$ (40 mg, 0.04 mmol, 0.1 equiv.) and triphenylphosphane (21 mg, 0.12 mmol, 0.3 Equiv.) were reacted according to method C in 1,4-dioxane (3 mL), wherein after filtering off the catalyst over Celite©, the crude product was concentrated under reduced pressure and then dissolved in absolute EtOH (3 mL), whereupon 4,4'-sulfonyldianiline (290 mg, 1.17 mmol, 3 equiv.) and one drop of concentrated HCl were added and the reaction according to method A was further reacted. The product was obtained as a yellow solid (46 mg, 0.1 mmol, 25%). $R_f$=0.3 (DCM/MeOH, 10:1). LC-MS: m/z=475.35 [M+H]$^+$. $^1$H NMR (DMSO-d$_6$, 400 MHz) δ ppm 9.21 (br. s., 1H), 7.80 (d, J=8.0 Hz, 2H), 7.74 (d, J=9.5 Hz, 1H), 7.56 (d, J=8.0 Hz, 4H), 7.44 (d, J=7.0 Hz, 2H), 7.09 (s, 1H), 6.64 (d, J=8.0 Hz, 2H), 6.16 (br. s, 2H), 3.80 (br. s., 4H), 3.25 (br. s., 4H), 2.48 (br. s., 3H). $^{13}$C NMR (DMSO-d$_6$, 101 MHz) δ ppm 160.4, 155.4, 153.2, 147.9, 139.8, 128.5, 126.1, 121.4, 119.6, 112.8, 103.4, 82.4, 65.8, 48.5, 25.0.

N-(4-((4-((2-methyl-6-morpholinoquinolin-4-yl)amino) phenyl)sulfonyl)phenyl)acetamide (40): To a solution of N-(4-((4-aminophenyl)sulfonyl)phenyl)-2-methyl-6-morpholinoquinolin-4-amine (39) (20 mg, 0.042 mmol, 1 equiv.) in pyridine (0.75 mL) was added Ac$_2$O (40 μL, 0.42 mmol, 10 equiv.) and catalytic amounts of DMAP and the reaction stirred for 30 h at RT. Column chromatography on silica gel (DCM/MeOH) afforded the desired product as a yellow solid (15.5 mg, 0.03 mmol, 71%). $R_f$=0.43 (DCM/MeOH, 10:1). LC-MS: m/z=517.4 [M+H]$^+$. HR-MS [M+H]$^+$=calculated 517.1904, found 517.19055 (+0.28134 ppm). $^1$H NMR (DMSO-d$_6$, 400 MHz) δ ppm 10.44 (s, 1H), 7.77-7.91 (m, 6H), 7.73 (d, J=8.8 Hz, 1H), 7.55 (d, J=9.3 Hz, 1H), 7.44 (d, J=9.3 Hz, 2H), 7.40 (d, J=3.0 Hz, 5H), 7.24 (d, J=3.0 Hz, 3H), 7.12 (s, 1H), 3.78 (br. s., 4H), 3.23 (br. s., 4H), 2.47 (s, 3H), 2.08 (s., 3H). $^{13}$C NMR (DMSO-d$_6$, 101 MHz) δ ppm 168.9, 147.8, 143.3, 136.4, 135.1, 128.8, 128.7, 128.6, 128.5, 118.7, 75.0, 65.8, 48.5, 23.9.

(4-Bromophenyl)(4-nitrophenyl)methanone (42): 4-nitrobenzoyl chloride (2.5 g, 13.5 mmol, 1 equiv.) and AlCl$_3$ (2.69 g, 20.2 mmol, 1.5 equiv.) were dissolved in bromobenzene (3.53 mL, 33.7 mmol, 2.5 equiv.) and stirred for 30 minutes at RT. Subsequently, the reaction mixture was heated to 100° C. over 1.5 h and stirred for a further 2 h. After cooling to RT, the reaction was precipitated onto ice-water, the resulting solid filtered off and washed with plenty of water to give the product as a pale brown solid (3.43 g, 11.21 mmol, 83%). $R_f$=0.81 (PE/EA, 1:1). $^1$H NMR (CDCl3, 400 MHz) δ ppm 7.93-7.96 (m, 4H), 7.49-7.52 (m, 4H). $^{13}$C NMR (CDCl$_3$, 101 MHz): δ ppm 193.4, 149.6, 142.0, 134.6, 131.7, 131.2, 130.3, 128.5, 123.3.

(4-Aminophenyl)(4-bromophenyl)methanone (43): To a solution of (4-bromophenyl)(4-nitrophenyl)methanone (42) (500 mg, 1.64 mmol, 1 equiv) in EtOH/DMSO (6:1.5 mL) was added Na$_2$S$_2$O$_4$ (1.67 g, 8.2 mmol, 5 equiv.) and the reaction stirred for 30 h at 85° C. The reaction mixture was concentrated under reduced pressure, EtOAc and saturated NaHCO$_3$ solution were added and the pH adjusted to 9 with NH$_4$OH. The aqueous phase was extracted three times with EtOAc and the combined organic phases were dried over MgSO$_4$. Column chromatography on silica gel (DCM/MeOH) afforded the desired product as a white solid (75 mg, 0.27 mmol, 17%). R$_f$=0.7 (PE/EA, 1:1). LC-MS: m/z=275.1 [M+H]$^+$. $^1$H NMR (DMSO-d$_6$, 400 MHz) δ ppm 7.69-7.72 (m, 2H), 7.50-7.55 (m, 4H), 6.59-6.62 (m, 2H), 6.23 (s, 2H). $^{13}$C NMR (DMSO-d$_6$, 101 MHz) δ ppm 192.3, 154.0, 138.1, 132.6, 131.2, 130.8, 124.7, 123.2, 112.6.

(4-Bromophenyl)(4-((6-methoxy-2-methylquinolin-4-yl)amino)phenyl)methanone (44): 4-chloro-6-methoxy-2-methylquinoline (7) (61 mg, 0.29 mmol, 1.1 equiv.) and N-(4-(4-aminophenyl)(4-bromophenyl)methanone (43) (65 mg, 0.27 mmol, 1 equiv.) were dissolved in absolute EtOH (3 mL), one drop of concentrated HCl was added and reacted according to Method A to give the product as a golden yellow solid (95 mg, 0.212 mmol, 76%). R$_f$=0.6 (DCM/MeOH, 10:1). LC-MS: m/z=447.05 [M+H]$^+$. $^1$H NMR (DMSO-d$_6$, 500 MHz) δ ppm 9.14 (br. s., 1H), 7.95 (s, 1H), 7.75-7.81 (m, 4H), 7.67 (d, J=8.8 Hz, 2H), 7.62 (s, 1H), 7.44 (d, J=8.8 Hz, 2H), 7.35 (dd, J=8.8, 2.9 Hz, 1H), 7.22 (s, 1H), 3.91 (s, 3H), 2.51 (s, 3H). $^{13}$C NMR (DMSO-d$_6$, 126 MHz) δ ppm 192.88, 162.0, 156.0, 136.8, 131.7, 131.3, 131.0, 128.9, 125.5, 121.0, 117.9, 101.0, 55.4, 35.5, 30.5.

(4-((6-Methoxy-2-methylquinolin-4-yl)amino)phenyl)(4-(pyridin-4-yl-amino)phenyl)methanone (45): (4-bromophenyl)(4-((6-methoxy-2-methylquinolin-4-yl)amino)phenyl)methanone (44) (20 mg, 0.045 mmol, 1 equiv), 4-aminopyridine (5.5 mg, 0.053 mmol, 1.2 equiv.), NaOtBu (6 mg, 0.064 mmol, 1.4 equiv.), Pd$_2$(dba)$_3$ (4.5 mg, 0.0045 mmol, 0.1 equiv.) and triphenylphosphane (2.3 mg, 0.013 mmol, 0.3 equiv.) were reacted according to Method C in 1,4-dioxane (1.5 mL) to give the product as a yellow solid (16 mg, 0.035 mmol, 78%). R$_f$=0.57 (DCM/MeOH, 10:1). LC-MS: m/z=231.3 [M+H]$^{2+}$. HR-MS [M+H]$^+$=calculated 461.1972, found 461.19782 (+1.33252 ppm). $^1$H NMR (DMSO-d$_6$, 400 MHz) δ ppm 9.40 (s, 1H), 8.31 (d, J=5.3 Hz, 2H), 7.74-7.85 (m, 5H), 7.69 (d, J=2.5 Hz, 1H), 7.48 (d, J=8.8 Hz, 2H), 7.31-7.40 (m, 3H), 7.19 (s, 1H), 7.07-7.14 (m, 2H), 3.92 (s, 3H), 2.45 ppm (s, 3H). $^{13}$C NMR (DMSO-d$_6$, 101 MHz) δ ppm 156.0, 155.6, 149.9, 148.6, 144.7, 131.4, 131.3, 130.7, 130.2, 121.3, 119.6, 118.7, 117.2, 110.6, 105.0, 101.1, 55.5, 24.2.

(4-((6-Methoxy-2-methylquinolin-4-yl)amino)phenyl)(4-(pyrimidin-4-yl-amino)phenyl)methanone (46): (4-bromophenyl)(4-((6-methoxy-2-methylquinolin-4-yl)amino)phenyl)methanone (44) (30 mg, 0.067 mmol, 1 equiv), 4-aminopyrimidine (8 mg, 0.081 mmol, 1.2 equiv.), NaOtBu (9 mg, 0.094 mmol, 1.4 equiv.), Pd$_2$(dba)$_3$ (6 mg, 0.006 mmol, 0.1 equiv.) and triphenylphosphane (3.5 mg, 0.018 mmol, 0.3 equiv.) were reacted according to Method C in 1,4-dioxane (1.5 mL) to give the product as a yellow solid (21 mg, 0.046 mmol, 69%). R$_f$=0.45 (DCM/MeOH, 10:1). LC-MS: m/z=462.35 [M+H]$^+$. HR-MS [M+H]$^+$=calculated 462.19245, found 462.1928 (+0.75802 ppm). $^1$H NMR (DMSO-d$_6$, 500 MHz) δ ppm 10.13 (s, 1H), 8.73 (s, 1H), 8.37 (d, J=5.7 Hz, 1H), 8.32 (s, 1H), 7.94 (d, J=8.8 Hz, 2H), 7.76-7.83 (m, 4H), 7.70 (d, J=2.3 Hz, 1H), 7.48 (d, J=8.8 Hz, 2H), 7.37 (dd, J=9.2, 2.7 Hz, 1H), 7.19 (s, 1H), 6.95 (dd, J=5.7, 2.7 Hz, 1H), 5.75 (s, 1H), 3.93 (s, 3H), 2.52 (s, 3H). $^{13}$C NMR (DMSO-d$_6$, 126 MHz) δ ppm 192.7, 174.2, 163.1, 159.4, 158.1, 157.7, 156.1, 155.5, 154.5, 143.5, 131.3, 130.7, 121.3, 118.2, 109.6, 54.7, 54.4, 24.2.

(4-Bromophenyl)(4-nitrophenyl)methanone (c): 4-nitrobenzoyl chloride (10 g, 53.9 mmol, 1 equiv.) and AlCl$_3$ (10.8 g, 80.8 mmol, 1.5 equiv.) were dissolved in bromobenzene (14.1 mL, 134 mmol, 2.5 equiv.) and stirred for 30 minutes at RT. Subsequently, the reaction mixture was heated to 100° C. over 1.5 h and stirred for a further 2 h. After cooling to RT, the reaction was precipitated onto ice-water, the resulting solid filtered off and washed with plenty of water to give the product as a pale brown solid (14.2 g, 46.4 mmol, 86%). H NMR (CHLOROFORM-d, 500 MHz): δ=7.94 (d, J=8.8 Hz, 4H), 7.51 ppm (d, J=8.8 Hz, 4H). $^{13}$C NMR (CHLOROFORM-d, 101 MHz): δ=193.4, 149.6, 142.0, 134.6, 131.7, 131.2, 130.3, 128.5, 123.3 ppm.

1-Bromo-4-(4-nitrobenzyl)benzene (d): To a solution of (4-bromophenyl)(4-nitrophenyl)methanone (1 g, 3.27 mmol, 1 equiv.) in DCM (10 mL) was added dropwise with stirring a solution of trifluoromethanesulfonic acid (540 μL, 6.11 mmol, 1, 8 equiv.) in DCM (4 mL) followed by the dropwise addition of a solution of triethylsilane (740, 4.63 mmol, 1.4 equiv.) in DCM (4 mL). The reaction was stirred at RT for 6 h and then poured onto a saturated Na$_2$CO$_3$ solution at 0° C., extracted three times with DCM and the combined organic phases were dried over MgSO$_4$ and the solvent was removed under reduced pressure. Column chromatography on silica gel (petroleum ether/EtOAc) afforded the product as a white solid (690 mg, 2.36 mmol, 72%). GC-MS: 290/292. $^1$H NMR (CHLOROFORM-d, 300 MHz): δ=8.11-8.20 (m, 2H), 7.41-7.51 (m, 2H), 7.28-7.35 (m, 2H), 7.05 (d, J=8.8 Hz, 2H), 4.04 ppm (s, 2H). $^{13}$C NMR (CHLOROFORM-d, 75 MHz): δ=148.5, 138.5, 132.3, 131.1, 130.0, 124.3, 121.1, 41.5 ppm.

4-(4-Bromobenzyl)aniline (e): To a solution of 1-bromo-4-(4-nitrobenzyl) benzene (650 mg, 2.23 mmol, 1 equiv) in EtOH/DMSO (10:2.5 mL) was added Na$_2$S$_2$O$_4$ (194 g, 11.1 mmol, 5 equiv.) and the reaction stirred for 24 h at 85° C. After cooling to RT, EtOH was removed from the reaction mixture under reduced pressure. The reaction was then precipitated onto ice-water, extracted three times with EtOAc and the combined organic phases dried over MgSO$_4$ and the solvent removed under reduced pressure. Column chromatography on silica gel (petroleum ether/EtOAc) afforded the product as an orange solid (335 mg, 1.28 mmol, 57%). GC-MS: 261/263.

N-(4-(4-Bromobenzyl)phenyl)-6-methoxy-2-methylquinolin-4-amine (g): To a solution of 4-chloro-2-methylquinoline (218 mg, 1.05 mmol, 1.1 equiv.) and 4-(4-bromobenzyl)aniline (230 mg, 0.88 mmol, 1 equiv) in absolute EtOH (4 mL) was added one drop of concentrated HCl and the reaction mixture was heated under reflux for 6 h. The reaction was concentrated under reduced pressure and the remaining residue was suspended in EtOAc and NH$_4$OH and stirred until all the solid had dissolved. The aqueous phase was extracted three times with EtOAc, the combined organic phases were dried over MgSO$_4$ and the solvent was removed under reduced pressure. Column chromatography on silica gel (petroleum ether/EtOAc) afforded the desired product as a white solid (320 mg, 0.74 mmol, 84%). LC-MS: 433/453. $^1$H NMR (DMSO-d$_6$, 500 MHz): δ=8.60 (s, 1H), 7.69 (d, J=8.8 Hz, 1H), 7.66 (d, J=2.7 Hz, 1H), 7.50 (d, J=8.4 Hz, 2H), 7.22-7.30 (m, 7H), 6.76 (s, 1H), 3.93 (s, 2H), 3.89 (s, 3H), 2.39 ppm (s, 3H). $^{13}$C NMR (DMSO-d$_6$, 75 MHz):

δ=156.0, 155.8, 146.9, 144.3, 141.0, 138.9, 135.8, 131.3, 131.0, 129.9, 129.6, 122.5, 120.8, 119.1, 118.7, 101.5, 101.0, 55.6, 24.9 ppm.

6-Methoxy-2-methyl-N-(4-(4-(pyridin-4-ylamino)benzyl)phenyl)quinolin-4-amine (63): In a baked-out Schlenk flask with stirrer bar, N-(4-(4-bromobenzyl)phenyl)-6-methoxy-2-methylquinolin-4-amine (20 mg, 0.046 mmol, 1 equiv.), aminopyridine (5.2 mg, 0.06 mmol, 1.2 equiv.), KOtBu (7.25 mg, 0.07 mmol) and Pd$_2$dba$_3$ (4 mg, 6 μmol, 10 mol %) and XPhos (9 mg, 18 μmol, 30 mol %) were weighed in and sealed with a septum. The flask was evacuated three times with argon, degassed, 1,4-dioxane (2.5 mL) was added, and the septum replaced with a glass stopper. The reaction mixture was then stirred at 80° C. for 24 h. After cooling to RT, the reaction was diluted with DCM, filtered through Celite© and taken up in saturated NaHCO$_3$ solution. The aqueous phase was extracted three times with DCM, the combined organic phases were dried over MgSO$_4$ and the solvent removed under reduced pressure. Column chromatography on silica gel (DCM/MeOH) afforded the product as a yellow solid (14 mg, 0.031 mmol, 68%). LC-MS: 224.2/447.3. $^1$H NMR (DMSO-d$_6$, 500 MHz): δ=8.99 (br. s., 1H), 8.15 (d, J=5.4 Hz, 1H), 8.03 (d, J=5.7 Hz, 1H), 7.83 (d, J=2.7 Hz, 1H), 7.76 (d, J=9.2 Hz, 1H), 7.29-7.37 (m, 4H), 7.25 (d, J=8.4 Hz, 2H), 7.16 (d, J=8.4 Hz, 2H), 6.89 (d, J=6.1 Hz, 1H), 6.74 (s, 1H), 6.67 (d, J=6.5 Hz, 1H), 3.88-3.97 (m, 5H), 2.42 ppm (s, 3H). 13C NMR (DMSO-d$_6$, 126 MHz): δ=157.3, 156.0, 154.9, 150.6, 149.0, 143.4, 138.0, 137.9, 137.1, 135.7, 131.6, 129.4, 122.9, 121.4, 120.5, 118.3, 108.7, 108.6, 101.4, 100.9, 55.7, 23.5 ppm.

6-Methoxy-2-methyl-N-(4-(4-(pyrimidin-4-ylamino)benzyl)phenyl)quinolin-4-amine (68): In a baked-out Schlenk flask with stirrer bar, N-(4-(4-bromobenzyl)phenyl)-6-methoxy-2-methylquinolin-4-amine (60 mg, 0.14 mmol, 1 equiv.), aminopyrimidine (17 mg, 0.18 mmol, 1.2 equiv.), KOtBu (22 mg, 0.21 mmol) and Pd$_2$dba$_3$ (12 mg, 18 μmol, 10 mol %) and XPhos (27 mg, 54 μmol, 30 mol %) were weighed in and sealed with a septum. The flask was evacuated three times with argon, degassed 1,4-dioxane (5 mL) was added, and the septum replaced with a glass stopper. The reaction mixture was then stirred at 80° C. for 24 h. After cooling to RT, the reaction was diluted with DCM, filtered through Celite© and taken up in saturated NaHCO$_3$ solution. The aqueous phase was extracted three times with DCM, the combined organic phases were dried over MgSO$_4$ and the solvent removed under reduced pressure. Column chromatography on silica gel (DCM/MeOH) afforded the product as a yellow solid (19 mg, 0.044 mmol, 31%). LC-MS: 448.1. $^1$H NMR (500 MHz, DMSO) δ=948; 9.58 (s, 1H), 8.83 (s, 1H), 8.59 (s, 1H), 8.24 (d, J=5.8 Hz, 1H), 7.79-7.67 (m, 2H), 7.61 (d, J=8.3 Hz, 2H), 7.36-7.27 (m, 5H), 7.24 (d, J=8.3 Hz, 2H), 6.83-6.71 (m, 2H), 3.92 (d, J=10.6 Hz, 5H), 2.42 (s, 3H). $^{13}$C NMR (126 MHz, DMSO) δ=948; 160.8, 158.8, 156.9, 156.4, 155.9, 147.3, 139.2, 138.5, 137.9, 136.4, 130.4, 129.8, 123.7, 122.1, 121.1, 119.4, 109.9, 107.8, 102.1, 70.6, 56.6, 25.1.

Investigations of the Efficacy of the Compounds According to the Invention and the Comparative Compound Inhibitory Activity Towards MtTrxR:

A biochemical evaluation of the inhibitory activity (i.e. the IC$_{50}$ value) of the compounds obtained towards MtTrxR by means of an activity assay according to Lu et al. (error range indicated by the standard deviation) was conducted. The testing of the potential inhibitors against MtTrxR was performed according to the description of Lu et al. Furthermore, MIC$_{50}$ values (generic minimum inhibitory concentration) of certain compounds were measured with the BD BACTEC™ MGIT™ system:

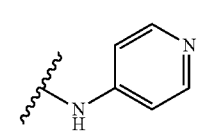

| Compound | R$^1$ | X | R$^2$ | IC$_{50}$ [μM] DTNB assay | MIC$_{50}$ [μM] (μG/mL) | cLogP |
|---|---|---|---|---|---|---|
| 1 (comparison) | MeO | OH | — | 11.54 ± 1.52 | n.d. ** | 3.77 |
| 2 | MeO | SO$_2$ | 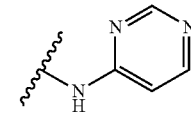 | 0.25 ± 0.04 | 8-32 | 5.18 |
| 8 | MeO | CH$_2$ | NH$_2$ | 1.80 ± 0.80 | 4-8 | 5.45 |
| 9 | MeO | SO$_2$ | NH$_2$ | 5.21 ± 0.24 | n.d. | 4.25 |
| 10 | MeO | SO$_2$ | NHAc | 3.59 ± 1.95 | n.d. | 3.96 |
| 24 | MeO | SO$_2$ | | 0.51 ± 0.04 | 8-32 | 5.30 |

-continued

| Compound | $R^1$ | X | $R^2$ | $IC_{50}$ [μM] DTNB assay | $MIC_{50}$ [μM] (μG/mL) | cLogP |
|---|---|---|---|---|---|---|
| 25 | MeO | $SO_2$ | (NH-pyrazole-tBu) | 9.1 ± 0.30 | n.d. | n.d. |
| 26 | MeO | $SO_2$ | (NH-phenyl-OMe) | 1.90 ± 0.80 | 8-32 | 6.39 |
| 27 | MeO | $SO_2$ | (NH-phenyl-COOMe) | 4.80 ± 1.60 | n.d. | 6.34 |
| 45 | MeO | CO | (NH-pyridine) | 1.04 ± 0.20 | >32 | 6.20 |
| 63 | MeO | $CH_2$ | (NH-pyridine) | 5.64 ± 1.73<br>4.70 ± 0.70 | 8-32 | 6.38 |
| 68 | MeO | $CH_2$ | (NH-pyrimidine) | 2.03 ± 0.65<br>1.70 ± 0.001 | 2-8 | 6.50 |

\* inhibitory effect apparent from concentrations of >10 μM
\*\* not determined

The data show that the most potent inhibitor was identified as compound 2 and, in addition, improved biological activity was achieved by acetylation of compound 9. A notable difference could be found for compound 8, having a better activity for which an $IC_{50}$ value of 1.8 μM was determined. This determination did not match the expected activity of 14.7 μM and was exceptional since it has been assumed that no alternative bridging group to a sulfone could achieve an improvement, but which was contradicted by the comparison of compound 8 and 10. The testing of the $CH_2$-bridged compound 8 thus afforded a promising candidate for further optimization since it was expected that the increase in lipophilicity by the methyl group should constitute improved permeability to the mycobacterial cell wall. The sulfone-bridged compounds 24, 25, 26 and 27 show loss of activity compared to compound 2, but are nevertheless more potent inhibitors than the comparative compound 1. The carbonyl-bridged compound 45 is also a more potential inhibitor than comparative compound 1. The $CH_2$-bridged compounds 63 and 68 are also more potent inhibitors than comparative compound 1.

Permeability:

Selected compounds were investigated in terms of their permeability with the aid of the PAMPA assay (Parallel Artificial Membrane Permeation Assay). The permeability of the compounds across an artificial membrane of phospholipids was tested in a filter plate. Since a significant difference existed between the artificial membrane and the mycobacterial cell wall, the values should only be used as a measure to be able to evaluate the permeability of the compounds with respect to each other. For this purpose, the distribution between a donor and acceptor chamber without membrane was determined as the reference value (100% flux), in which the concentration of the compounds in the chambers was determined spectrophotometrically. Subsequently, the permeability of compounds 1, 8, 63 and 68 across the membrane used was determined. The PAMPA flux [%] value was 12.60 for compound 1, 29.70 for compound 8, 53.60 for compound 63, and 41.00 for compound 68. It can be stated that compounds 8, 63 and 68 have a significantly higher permeability than comparative compound 1.

Antimycobacterial Activity:

Figure 1:
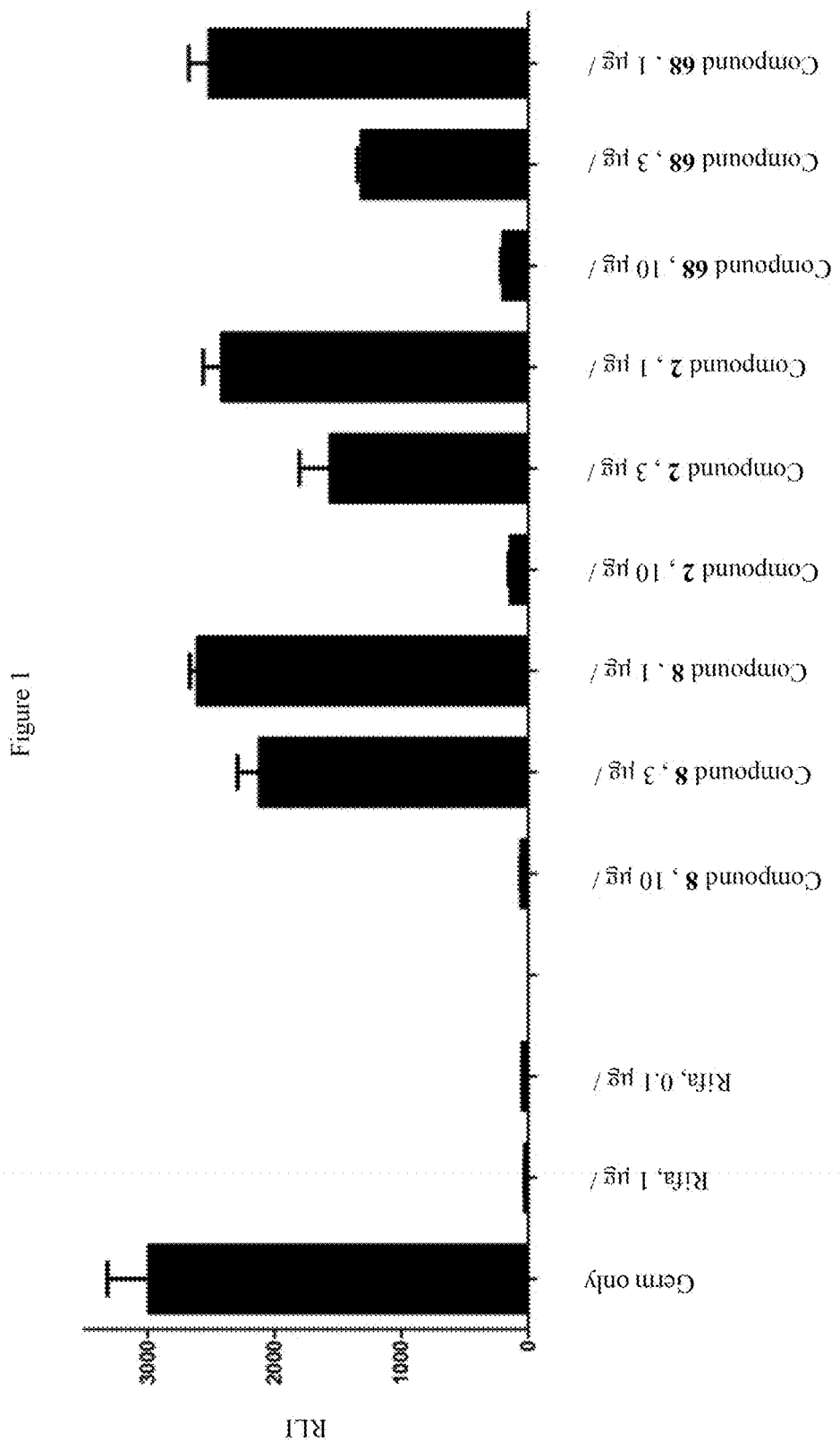
FIG. 1 shows that compounds according to the invention 2, 8 and 68 have a concentration-dependent antimycobacterial activity.
Figure 2:
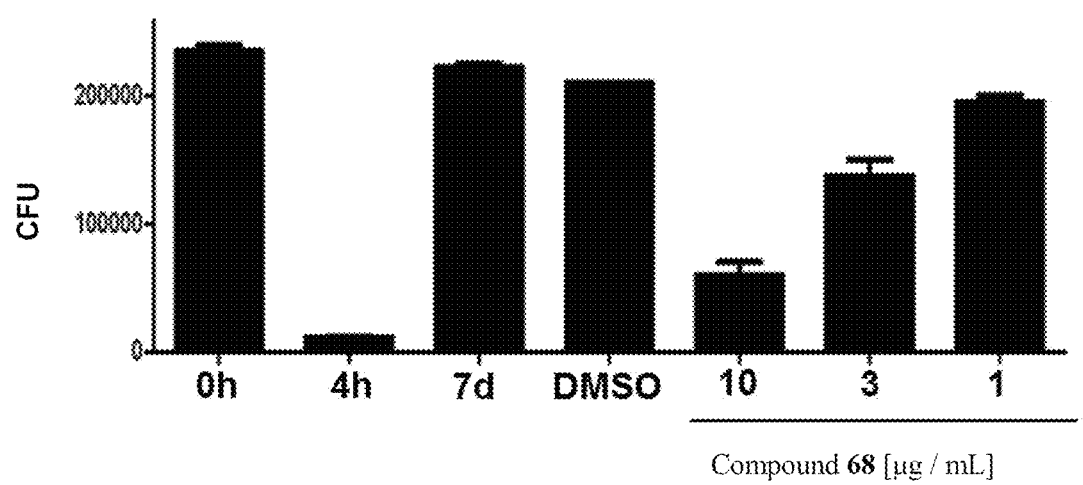
FIG. 2 shows that compound 68 according to the invention has a concentration-dependent antimycobacterial activity on the *Mycobacterium tuberculosis* strain H37Rv in infected human macrophages.
Figure 3:
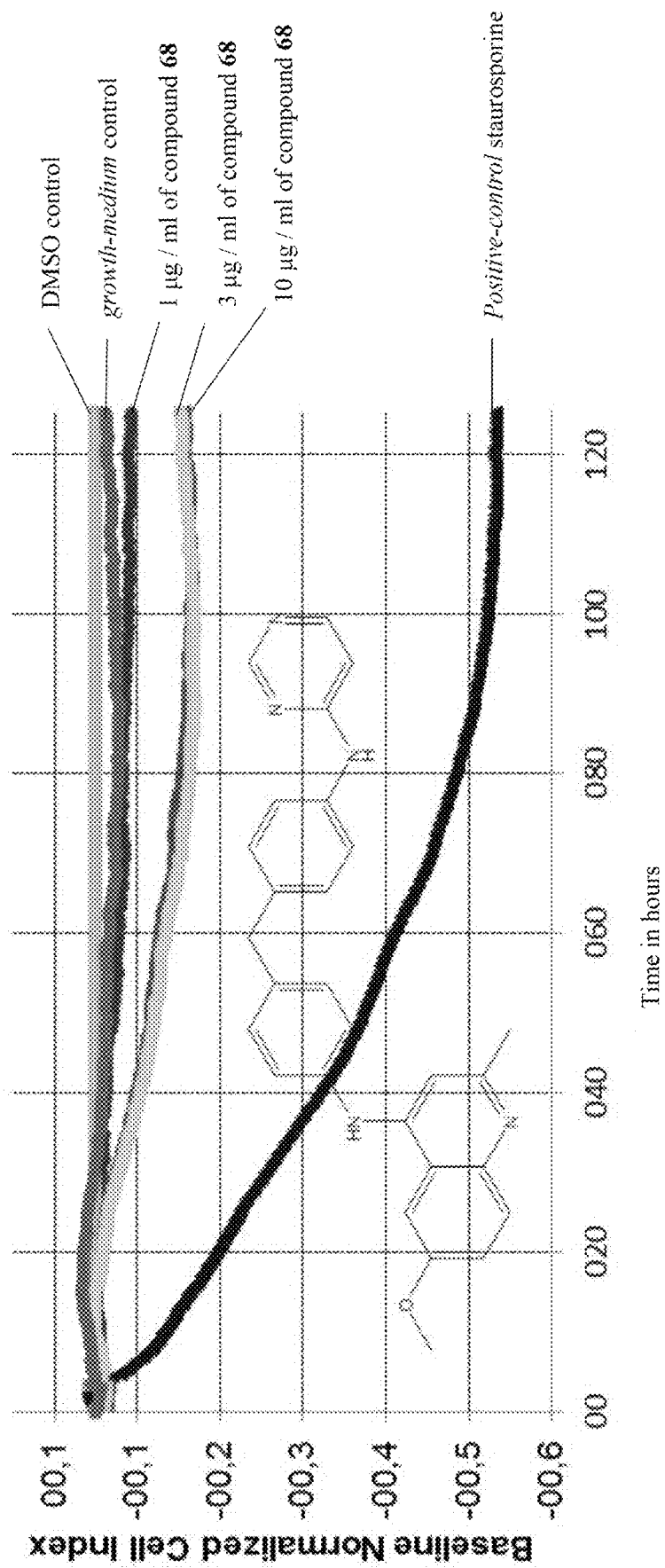

Cytotoxicity:

FIG. 3 shows that compound 68 according to the invention has a concentration-dependent growth inhibition in infected macrophages without influencing the macrophages, i.e. without being toxic.

The invention claimed is:

1. A compound which is selected from the group consisting of:

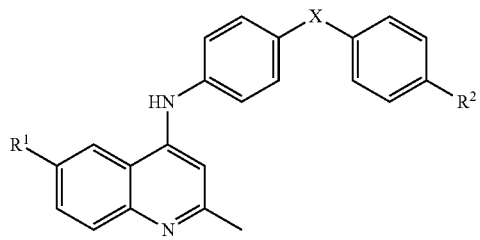

6-methoxy-2-methyl-N-(4-((4-(pyridin-4-ylamino)phenyl)sulfonyl)phenyl)quinolin-4-amine (2):

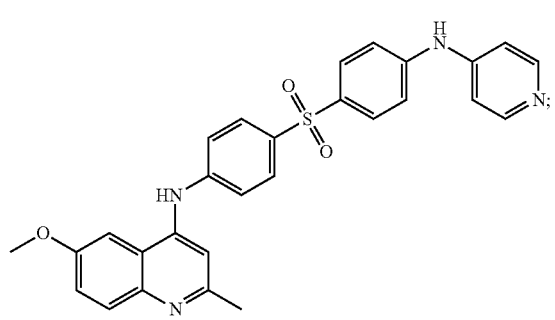

N-(4-((4-aminophenyl)sulfonyl)phenyl)-6-methoxy-2-methylquinolin-4-amine (9):

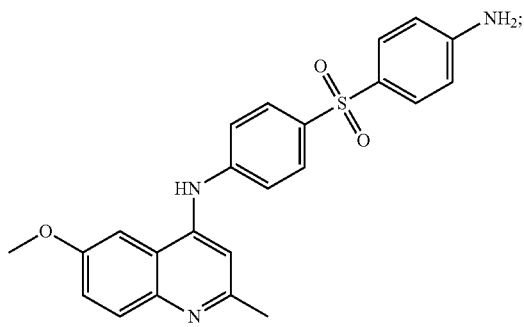 [SMILES: COc1ccc2nc(C)cc(Nc3ccc(S(=O)(=O)c4ccc(N)cc4)cc3)c2c1]

N-(4-((4-((6-methoxy-2-methylquinolin-4-yl)amino)phenyl)sulfonyl)phenyl)acetamide (10):

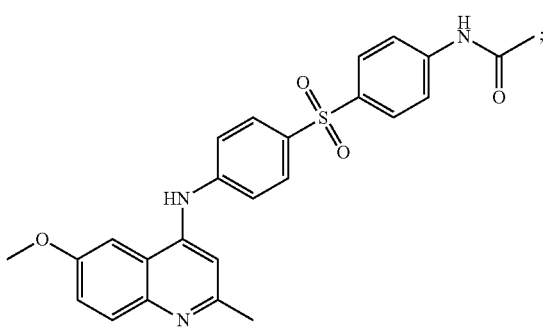 [SMILES: COc1ccc2nc(C)cc(Nc3ccc(S(=O)(=O)c4ccc(NC(C)=O)cc4)cc3)c2c1]

6-methoxy-2-methyl-N-(4-((4-(pyrimidin-4-yl-amino)phenyl)sulfonyl)phenyl)quinolin-4-amine (24):

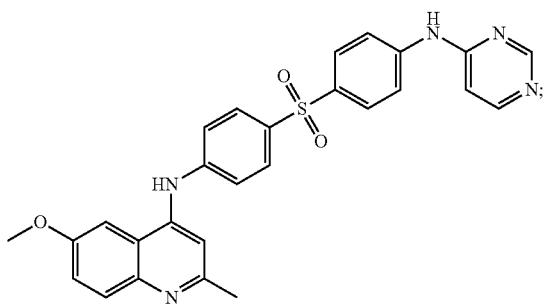 [SMILES: COc1ccc2nc(C)cc(Nc3ccc(S(=O)(=O)c4ccc(Nc5ccncn5)cc4)cc3)c2c1]

N-(4-((4-((3-(tert-butyl)-1H-pyrazol-5-yl)amino)phenyl)sulfonyl)phenyl)-6methoxy-2-methylquinolin-4-amine (25):

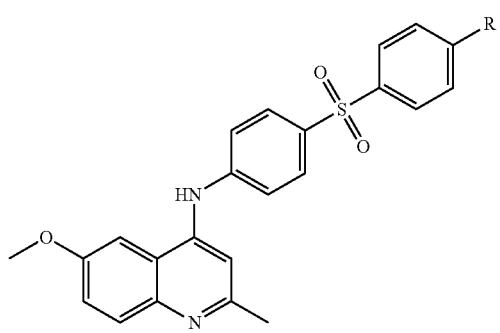

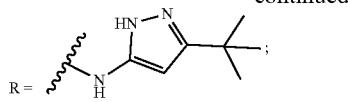

6-methoxy-N-(4-((4-((4-methoxyphenyl)amino)phenyl)sulfonyl)phenyl)-2-methylquinolin-4-amine (26):

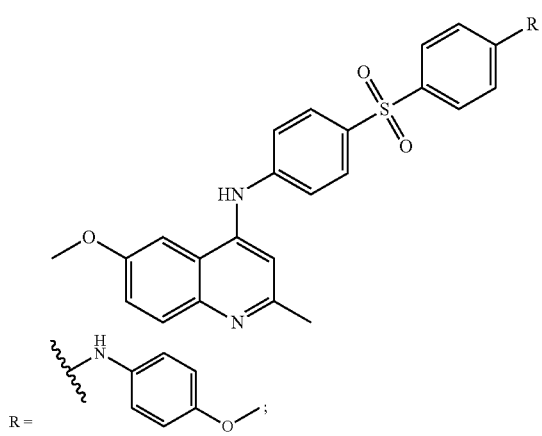

methyl-4-((4-((4-(((6-methoxy-2-methylquinolin-4-yl)amino)phenyl)sulfonyl)phenyl)amino) benzoate (27):

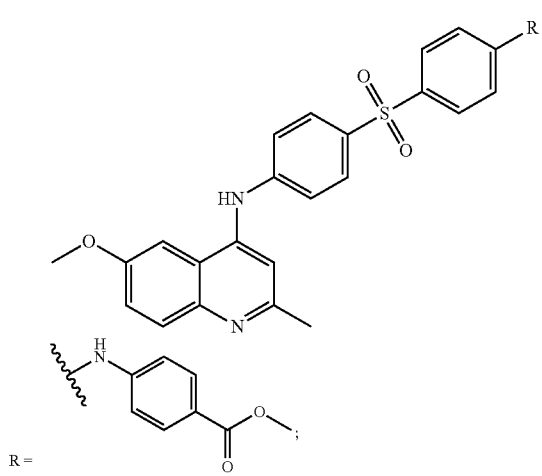

(4-((6-methoxy-2-methylquinolin-4-yl)amino)phenyl)(4-(pyridin-4-yl-amino) phenyl)methanone (45):

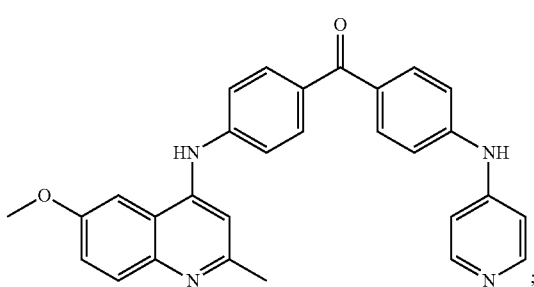 [SMILES: COc1ccc2nc(C)cc(Nc3ccc(C(=O)c4ccc(Nc5ccncc5)cc4)cc3)c2c1]

6-methoxy-2-methyl-N-(4-(4-(pyridin-4-ylamino)benzyl)phenyl)quinolin-4-amine (63):

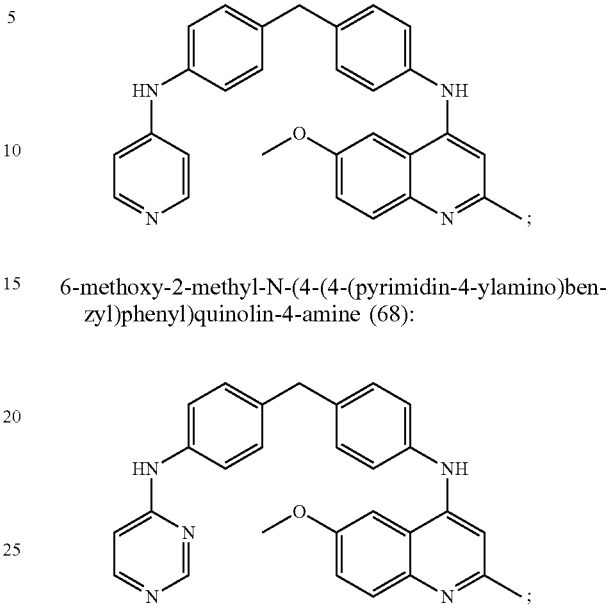

6-methoxy-2-methyl-N-(4-(4-(pyrimidin-4-ylamino)benzyl)phenyl)quinolin-4-amine (68):

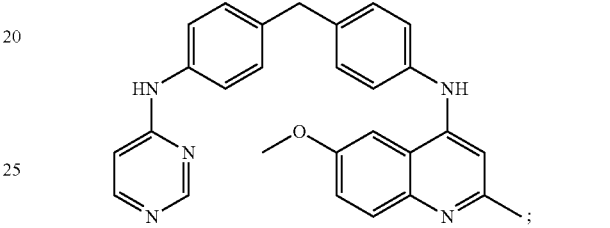

and
physiologically acceptable salts thereof.

2. A medicament comprising at least one compound as claimed in claim 1 or a physiologically acceptable salt thereof, and optionally suitable additives and/or auxiliaries and/or optionally further active ingredients.

3. The compound as claimed in claim 1 for use as a medicament.

4. The compound as claimed in claim 1, for use in the treatment of tuberculosis.

5. The compound as claimed in claim 4 for use in the treatment of tuberculosis, wherein tuberculosis is selected from the group consisting of
  tuberculosis of the respiratory organs,
  tuberculosis of the nervous system,
  tuberculosis of other organs, and
  miliary tuberculosis.

6. The compound as claimed in claim 5 for use in the treatment of tuberculosis, wherein
  tuberculosis of he respiratory organs is selected from the group consisting of
    pulmonary tuberculosis,
    tuberculosis of the intrathoracic lymph nodes,
    tuberculosis of the larynx, trachea and bronchi, and
    tuberculous pleurisy;
  tuberculosis of the nervous system is selected from the group consisting of
    tuberculous meningitis, and
    meningeal tuberculoma;
  tuberculosis of other organs is selected from the group consisting of
    tuberculosis of bones and joints,
    tuberculosis of the genitourinary system,
    tuberculosis of peripheral lymph nodes,
    tuberculosis of the intestine, peritoneum and mesenteric lymph nodes, tuberculosis of the skin and subcutaneous tissue,
tuberculosis of the eye,
tuberculosis of the ear, and
tuberculosis of the adrenal glands.

* * * * *